US012734000B2

(12) United States Patent
Weiman et al.

(10) Patent No.: US 12,734,000 B2
(45) Date of Patent: Sep. 15, 2026

(54) COMPUTER ASSISTED SURGERY NAVIGATION USING INTRA-OPERATIVE TACTILE SENSING FEEDBACK THROUGH MACHINE LEARNING SYSTEM

(71) Applicant: GLOBUS MEDICAL, INC., Audubon, PA (US)

(72) Inventors: Mark Weiman, Downingtown, PA (US); Myles Sullivan, Philadelphia, PA (US); Carly Taubenkraut, Perkasie, PA (US); Corbett McLaughlin, Bryn Mawr, PA (US)

(73) Assignee: Globus Medical, Inc., Audubon, PA (US)

( * ) Notice: Subject to any disclaimer, the term of this patent is extended or adjusted under 35 U.S.C. 154(b) by 552 days.

(21) Appl. No.: 18/157,192

(22) Filed: Jan. 20, 2023

(65) Prior Publication Data

US 2024/0245474 A1 Jul. 25, 2024

(51) Int. Cl.

| | |
|---|---|
| ***A61B 34/32*** | (2016.01) |
| ***A61B 34/00*** | (2016.01) |
| ***A61B 34/10*** | (2016.01) |
| ***A61B 34/20*** | (2016.01) |

(52) U.S. Cl.

CPC .............. *A61B 34/32* (2016.02); *A61B 34/10* (2016.02); *A61B 34/20* (2016.02); *A61B 34/25* (2016.02); *A61B 2034/107* (2016.02); *A61B 2034/2048* (2016.02); *A61B 2034/254* (2016.02)

(58) Field of Classification Search

CPC ......... A61B 34/32; A61B 34/10; A61B 34/20; A61B 34/25; A61B 2034/107; A61B 2034/2048; A61B 2034/254

See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |

(Continued)

OTHER PUBLICATIONS

US 8,231,638 B2, 07/2012, Swarup et al. (withdrawn)

*Primary Examiner* — Jay Khandpur
*Assistant Examiner* — Thomas E Worden

(57) ABSTRACT

A surgery navigation system is disclosed for computer assisted navigation during surgery. The surgery navigation system includes processing circuitry that is operative to obtain from a sensor circuit, intra-operative tactile sensing data indicating a sensed characteristic of a tool contacting a location on patient anatomy within a surgical site. The processing circuitry is further operative to process the intra-operative tactile sensing data through a machine learning model to generate intra-operative navigated guidance data, and to provide the intra-operative navigated guidance data to a display device and/or to a surgical robot to control movement of the tool.

20 Claims, 15 Drawing Sheets

(56) References Cited

U.S. PATENT DOCUMENTS 5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.

(56) References Cited

U.S. PATENT DOCUMENTS 7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Williams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jenser
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Issacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.

(56) References Cited

U.S. PATENT DOCUMENTS 8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois

(56) References Cited

U.S. PATENT DOCUMENTS

2008/0108991 A1 5/2008 von Jako
2008/0109012 A1 5/2008 Falco et al.
2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.

(56) References Cited

U.S. PATENT DOCUMENTS

2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.
2022/0047402 A1* 2/2022 Casey .................... A61B 90/98
2023/0054209 A1* 2/2023 Roh ........................ G16H 20/40
2023/0065449 A1* 3/2023 Torrie .................. A61B 17/152
2023/0157757 A1* 5/2023 Braido .................. G06T 19/003
345/419
2023/0339109 A1* 10/2023 Balicki .................. B25J 13/085
2024/0148455 A1* 5/2024 Donovan ............... A61B 34/30
2025/0009465 A1* 1/2025 Dumpe .................. G16H 40/63
2025/0143809 A1* 5/2025 Saxena .................. A61B 34/30
2025/0339220 A1* 11/2025 Brubaker ............... A61B 34/10

* cited by examiner

COMPUTER ASSISTED SURGERY NAVIGATION USING INTRA-OPERATIVE TACTILE SENSING FEEDBACK THROUGH MACHINE LEARNING SYSTEM

FIELD

The present disclosure relates to medical devices and systems, and more particularly, providing navigation information to surgeons and/or surgical robots for computer assisted navigation during spinal surgery.

BACKGROUND

There are a numerous types of spinal surgery procedures, including vertebroplasty and kyphoplasty, spinal laminectomy or spinal decompression, discectomy, foraminotomy, spinal fusion, and disk replacement. Patient satisfaction with the outcome of spinal surgery can depend upon the surgeon's expertise with best practices and use of rapidly emerging innovations in surgical procedures, new and customized implant designs, computer-assisted navigation, and surgical robot systems.

For example, the post-operative outcome for patient from spinal surgery can be improved through inter-operative actions which incise, dissect, or otherwise disturb patient anatomy only to the extent defined by a surgical plan. Failure to do so may result in iatrogenic pathologies and unwanted complications. It is therefore beneficial to fully understand the biological components of the anatomy at a surgical site. Currently, pre-operative and/or intra-operative imaging can be provided to surgeons to help navigate surgery procedures and enable more direct visualization of the intra-operative progress of the surgery. Image based navigation may be used in conjunction with robotic navigation to follow a more ideal path through patient anatomy. These navigation approaches can be subject to limitations which should be addressed to reduce unnecessary disturbance of patient anatomy during surgery on the spine and other locations and anatomy of patients.

SUMMARY

Some embodiments of the present disclosure are directed to a surgery navigation system for computer assisted navigation during surgery. The surgery navigation system includes processing circuitry that is operative to obtain from a sensor circuit, intra-operative tactile sensing data indicating a sensed characteristic of a tool contacting a location on patient anatomy within a surgical site. The processing circuitry is further operative to process the intra-operative tactile sensing data through a machine learning model to generate intra-operative navigated guidance data, and to provide the intra-operative navigated guidance data to a display device and/or to a surgical robot to control movement of the tool.

In some further embodiments, the intra-operative navigated guidance data can indicate any one or more of: level of force between the tool and the location on the patient anatomy; level of torque between the tool and the location on the patient anatomy; vibration characteristic of the tool working at the location on the patient anatomy; sound characteristic of the tool working at the location on the patient anatomy; and electrical charge transfer characteristic and/or impedance characteristic between the tool and the location on the patient anatomy.

Some other embodiments are directed to a corresponding method by a surgery navigation system for computer assisted navigation during surgery. Some other embodiments are directed to a corresponding computer program product for a surgery navigation system for computer assisted navigation during surgery.

Other surgery navigation systems and corresponding methods and computer program products according to embodiments will be or become apparent to one with skill in the art upon review of the following drawings and detailed description. It is intended that all such surgery navigation systems, methods, and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 5-8 an overhead view of a surgical system arranged during a surgical procedure in a surgical room which includes a camera tracking system for computer assisted navigation during surgery and which may further include a surgical robot for robotic assistance according to some embodiments;

DETAILED DESCRIPTION

Figure 1:
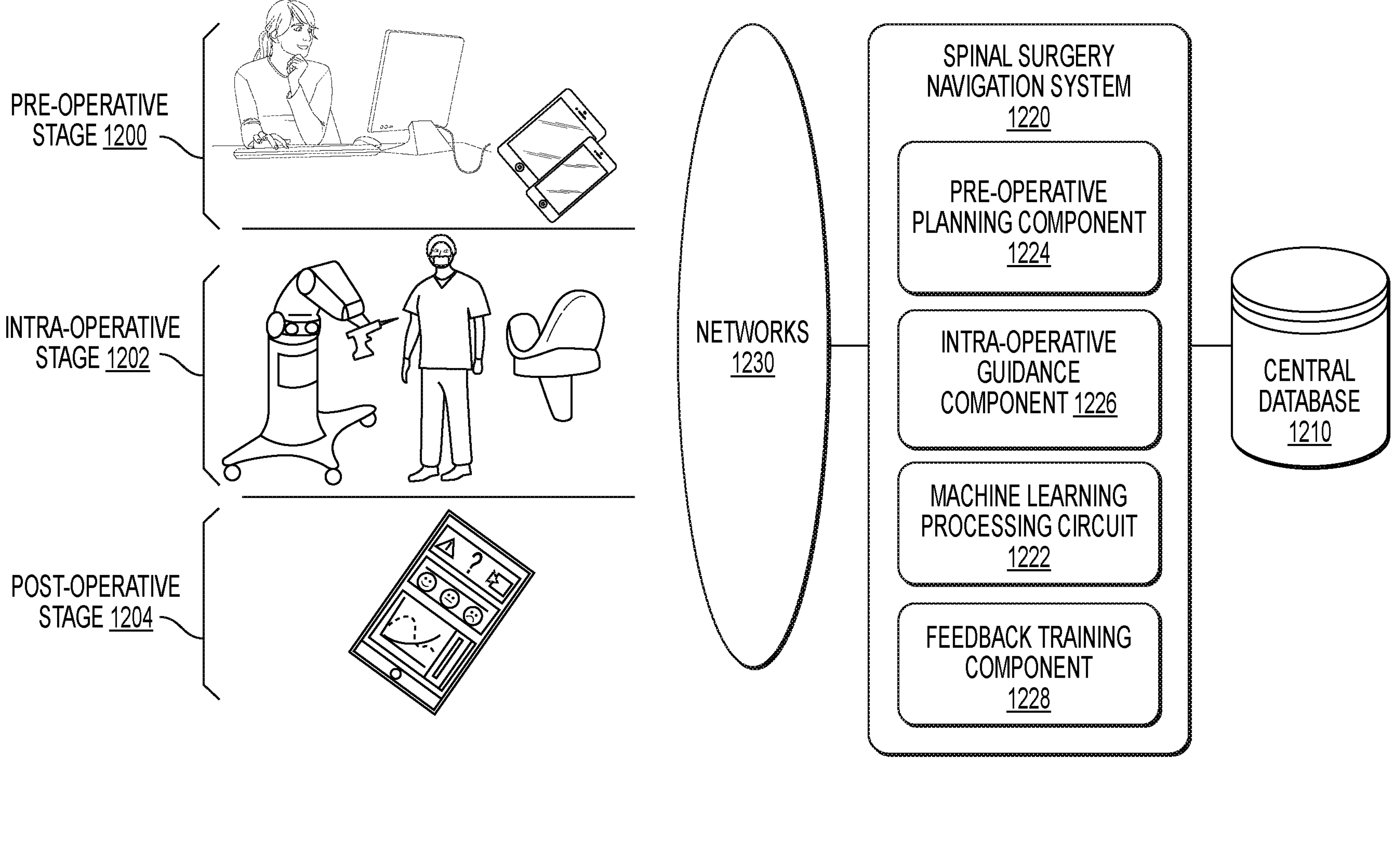
FIG. 1 illustrates a navigated spinal surgery workflow which uses a spinal surgery navigation system configured in accordance with some embodiments.

Inventive concepts will now be described more fully hereinafter with reference to the accompanying drawings, in which examples of embodiments of inventive concepts are shown. Inventive concepts may however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Embodiments of the present disclosure are directed to improving surgery outcomes through use of one or more sensor circuits which output intra-operative tactile sensing data indicating a sensed characteristic of a tool contacting a location on patient anatomy within a surgical site. The intra-operative tactile sensing data is processed through a machine learning model to generate intra-operative navigated guidance data. The intra-operative navigated guidance data is provided to a display device and/or to a surgical robot to control movement of the tool during the surgical procedure.

As will be explained in further detail below, the sensor circuit(s) may include any one or more of:

- a force sensor operative to output an indication of level of force between the tool and the location on the patient anatomy;
- a torque sensor operative to output an indication of level of torque between the tool and the location on the patient anatomy;
- a vibration sensor operative to output a vibration characteristic of the tool working at the location on the patient anatomy;
- a sound sensor operative to output a sound characteristic of the tool working at the location on the patient anatomy; and
- an electrical sensor operative to output an electrical charge transfer characteristic and/or an impedance characteristic between the tool and the location on the patient anatomy.

The machine learning model may be configured to process the intra-operative tactile sensing data to identify and differentiate between contact with bone, cartilage, ligaments, or other soft tissue including but not limited to the nucleus pulposus and annulus fibrosis. The resulting intra-operative navigated guidance data can be coupled with anatomical location knowledge to provide tissue differentiation data sets that for computer assisted navigation during surgery and introduce tactility as an additional sense to artificial intelligence. Surgical navigation guidance provided to surgeons and/or to surgical robots can thereby be made more robust through a feedback loop using the intra-operative tactile sensing data.

These operational capabilities can benefit both surgeons and patients during surgical procedures, such as interbody fusion procedures and other spinal surgeries as will be described in further detail below.

Various surgery navigation systems, surgical robot systems, and other systems are now explained which can be used in combination with embodiments of the present disclosure. Subsequently, further detailed explanation is provided for surgical navigation systems, sensor circuits which output intra-operative tactile sensing data, and operations for training machine learning models to process intra-operative tactile sensing data to provide various types of intra-operative navigated guidance data, in accordance with some embodiments of the present disclosure.

Example questions and problems that exist in current lumbar interbody fusion procedures, include:

- How to make it patient specific and standardized concurrently?
- What is the targeted correction needed for best patient outcome based on presentation?
- What is the best approach (anterior, posterior, lateral, etc.) for the best patient outcome?
- How much direct decompression is needed versus how much indirect decompression is needed? How to address foraminal vs central stenosis?
- How effective or "complete" is the discectomy?
- Surgeon cognitive load
- Longer planning time and OR time There are multiple technique combinations and solutions for the same patient presentation, and there is variance among surgeons on which technique or approach would be chosen for the best patient outcome. This results in some variation in actual patient outcomes.

Embodiments of the present disclosure can address various of these questions and problems, by streamlining planning and surgical workflows, and identifying and using correlations to standardize patient outcomes. Some embodiments are directed to using integrated spine models which are trained by machine learning.

Some embodiments of the present disclosure are directed to spinal surgery navigation systems for computer assisted navigation during spinal surgery. The system processes numerous different types of inputs and continued data collection using artificial intelligence through machine learning models to find correlations between different patient presentations and their outcomes, cause and effect of various spine surgery elements (direct vs indirect decompression and degree of either, different approaches, actual amount of correction achieved per technique and implants used, etc.) to continually optimize AI-assisted spine surgery plans for better patient outcomes.

To establish a spine model and predictive algorithm to further support surgeon decision making in lumbar interbody fusion surgery, and improve patient outcomes, data is needed from multiple sources as first an initial baseline, and then to continually update and improve the spine model with machine learning.

Key points and planes of anatomy (e.g. pedicle cross sections, canal perimeters, foraminal heights, facet joints, superior/inferior endplates, intervertebral discs, vertebral body landmarks, etc.) derived from specific patient scans, allows the opportunity to generate a segmented spine model that can be used to auto-calculate pre-operative spinal alignment parameters. In addition, pre-operative data collection from literature, studies, physician key opinion leaders, existing electronic health records can be combined with other data pulled from the patient's scans (e.g. bone density, spine stiffness, etc.) to compile all the factors in order to determine the best path forward in terms of surgical intervention. With these inputs and continually trained spine models, the system can begin to draw correlations between patients and outcomes. Examples of data that can be collected as inputs and derived during the pre-operative stages are discussed below.

The spinal surgery navigation systems can include processing circuitry that executes computer software to perform operations that can accurately detect key points of anatomy derived from specific patient scans. The computer software may generate a segmented spine model that can be used to calculate pre-operative spinal alignment parameters, and (through machine learning, anatomical standards, pre/intra/post-operative data collection, and known patient outcomes) generate a machine learning model that can provide predictive surgical outcomes for a defined patient.

The predictive surgical outcomes can have sufficient accuracy to be relied upon for determining or suggesting possible diagnoses and/or determining ideal surgery access approach(es), degree of decompression needed (indirect and/or direct), required interbody size/placement, custom interbody expansion set points (height and lordosis), and fixation type/size/placement that would be required for the most ideal spinal correction and patient outcomes. The need for this type of capability ranges from complex spinal deformity cases to single level degenerative spinal cases, e.g., Interlaminar Lumbar Instrumented Fusion (ILIF) procedure, and may be beneficial for numerous types of spinal correction surgery including vertebral body replacements and disc replacements.

In some embodiments, the computer software accesses patient data in electronic health records (EHR) to operate to establish baseline data for a spine model for the patient. Patient data contained in an EHR may include, but is not limited to, patient demographics, patient medical history, diagnoses, medications, patient scans, known allergies, lab results, and doctor's notes. The computer software may utilize machine learning model algorithms and operations for pre-operative (pre-op) and/or intra-operative (intra-op) surgical planning. These operations can reduce user input needed to setup patient profiles, and allow for continual seamless data synchronization.

This and other operational functionality can be provided by a spinal surgery navigation system for computer assisted navigation during spinal surgery. In accordance with some embodiments, the spinal surgery navigation system include processing circuitry that is operative to obtain intra-operative feedback data and/or post-operative feedback data regarding spinal surgery outcome for a plurality of patients, and to train a machine learning model based on the intra-operative feedback data and/or the post-operative feedback date. The processing circuitry is further operative to obtain pre-operative patient data characterizing a spine of a defined-patient, generate a spinal surgery plan for the defined-patient based on processing the pre-operative patient data through the machine learning model, and provide the spinal surgery plan to a display device for review by a user.

Elements of the processing circuitry which obtain the intra-operative feedback data and/or post-operative feedback data and which train the machine learning model may be the same as or different than elements of the processing circuitry which obtain the pre-operative patient data, generate the spinal surgery plan, and provide the spinal surgery plan to the display device. The processing circuitry may include one or processors which execute software instructions in one or more memories and/or may include application specific integrated circuits. Multiple processors may be collocated and interconnected on a common substrate or common backplane or may be geographically distributed and communicatively connected through one or more local and/or wide-area communication networks.

Various embodiments disclosed herein are directed to improvements in operation of a spinal surgery navigation system providing navigated guidance when planning for and performing spinal surgical procedures, such as Interlaminar Lumbar Instrumented Fusion (ILIF) procedure, and spinal correction surgery which may include vertebral body replacement and/or disc replacement. A spinal surgery navigation system includes a machine learning model that can be trained and configured to provide patient customized guidance during pre-operative stage planning, intra-operative stage surgical procedures, and post-operative stage assessment. A database, e.g., centralized database, can store data that can be obtained in each of the stages across all patients who have previously used or are currently using the spinal surgery navigation system. The machine learning model can be trained over time based on data from the database so that the patient customized guidance provides improved surgical outcomes.

Training of the machine learning model can include training based on learned correlations between patient data and surgical outcomes, correlations between cause and effect of various spine surgery elements including, for example, direct versus indirect spine decompression and amount (degree) of either, differences between spinal surgery techniques, actual amount of spinal correction achieved as a function of particular spinal surgery technique and surgical implants used, etc. Training of the machine learning model may be performed repetitively, e.g., continually when new data is obtained, in order further improve surgical outcomes obtained by the spinal surgery plans generated from the machine learning model.

The machine learning model can use artificial intelligence techniques and may include a neural network model. The machine learning model may use centralized learning or federated learning techniques.

FIG. 1 illustrates a navigated spinal surgery workflow which uses a spinal surgery navigation system 1220 configured in accordance with some embodiments. Referring to FIG. 1, three stages of workflow are illustrated: pre-operative stage 1200; intra-operative stage 1202; and post-operative stage 1204. During the pre-operative stage 1200, a user (e.g., surgeon) generates a surgical plan (case) based on analyzed patient images with assistance from the spinal surgery navigation system 1220. During the intra-operative stage 1202, the spinal surgery navigation system 1220 uses a spinal surgery plan to provide navigated surgical assistance to the user, which may include displaying information and/or graphical indications to guide the user's actions, and/or provide instructions to guide a surgical robot 4 for precise plan execution. During the post-operative stage 1204, post-operative feedback data characterizing surgery outcomes is collected by the spinal surgery navigation system 1220, such as by patient measurements and/or patient surveys, etc. Data obtained across all phases 1200-1204 can be stored in a central database 1210 for use by the spinal surgery navigation system 1220 to train a machine learning model of a machine learning processing circuit 1222. The machine learning model can include artificial intelligence (AI) processes, neural network components, etc. The machine learning model can be initially trained and then further trained over time to generate more optimal spinal surgery plans customized for patients that result in improved surgical outcomes. Further example types of data that can be collected during the pre-operative stage 1200, intra-operative stage 1202, and post-operative stage 1204 are discussed further below with regard to, e.g., FIG. 3.

The example spinal surgery navigation system 1220 shown in FIG. 1 includes a pre-operative planning component 1224, an intra-operative guidance component 1226, a machine learning processing circuit 1222, and a feedback training component 1228.

As will be explained in further detail below, the feedback training component 1228 is configured to obtain post-operative feedback data which may be provided by distributed networked computers regarding surgical outcomes for a plurality of patients, and to train a machine learning model based on the post-operative feedback data. Although FIG. 1 shows a single computer, e.g., smart phone, providing post-operative feedback data during the post-operative stage 1204 through one or more networks 1230 (e.g., public (Internet) networks and or private networks) to the spinal surgery navigation system 1220 for storage in the central database 1210, it is to be understood that numerous network computers (e.g., hundreds of computers) could provide post-operative feedback data for each of many patients to the spinal surgery navigation system 1220 (i.e., to the feedback training component 1228) for use in training the machine learning model. Moreover, as explained in further detail below, the feedback training component 1228 can further train the machine learning model based on pre-operative data obtained during the pre-operative stage 1200 for numerous patients and based on intra-operative data obtained during the intra-operative stage 1202 for numerous patients. For example, the training can include adapting rules of a machine learning (e.g., artificial intelligence) algorithm, rules of one or more sets of decision operations, and/or weights and/or firing thresholds of nodes of a neural network model, to drive one or more defined key performance surgical outcomes indicated by the pre-operative data and/or the intra-operative data toward one or more defined thresholds or other rule(s) being satisfied.

The pre-operative planning component 1224 obtains pre-operative data from one or more computers which characterizes a defined-patient, and generates a spinal surgery plan for the defined-patient based on processing the pre-operative data through the machine learning model. The pre-operative planning component 1224 provides the spinal surgery plan to a display device for review by a user. Accordingly, the pre-operative planning component 1224 of the machine learning processing circuit 1222 generates a spinal surgery plan for a defined-patient using the machine learning model which has been trained based on the post-operative feedback data regarding surgical outcomes for the plurality of patients. The training of the machine learning model can be repeated as more post-operative feedback is obtained by the feedback training component 1228 so that the spinal surgery plans that are generated will become more continuous improved at providing more optimal surgical outcomes for patients.

Figure 2:
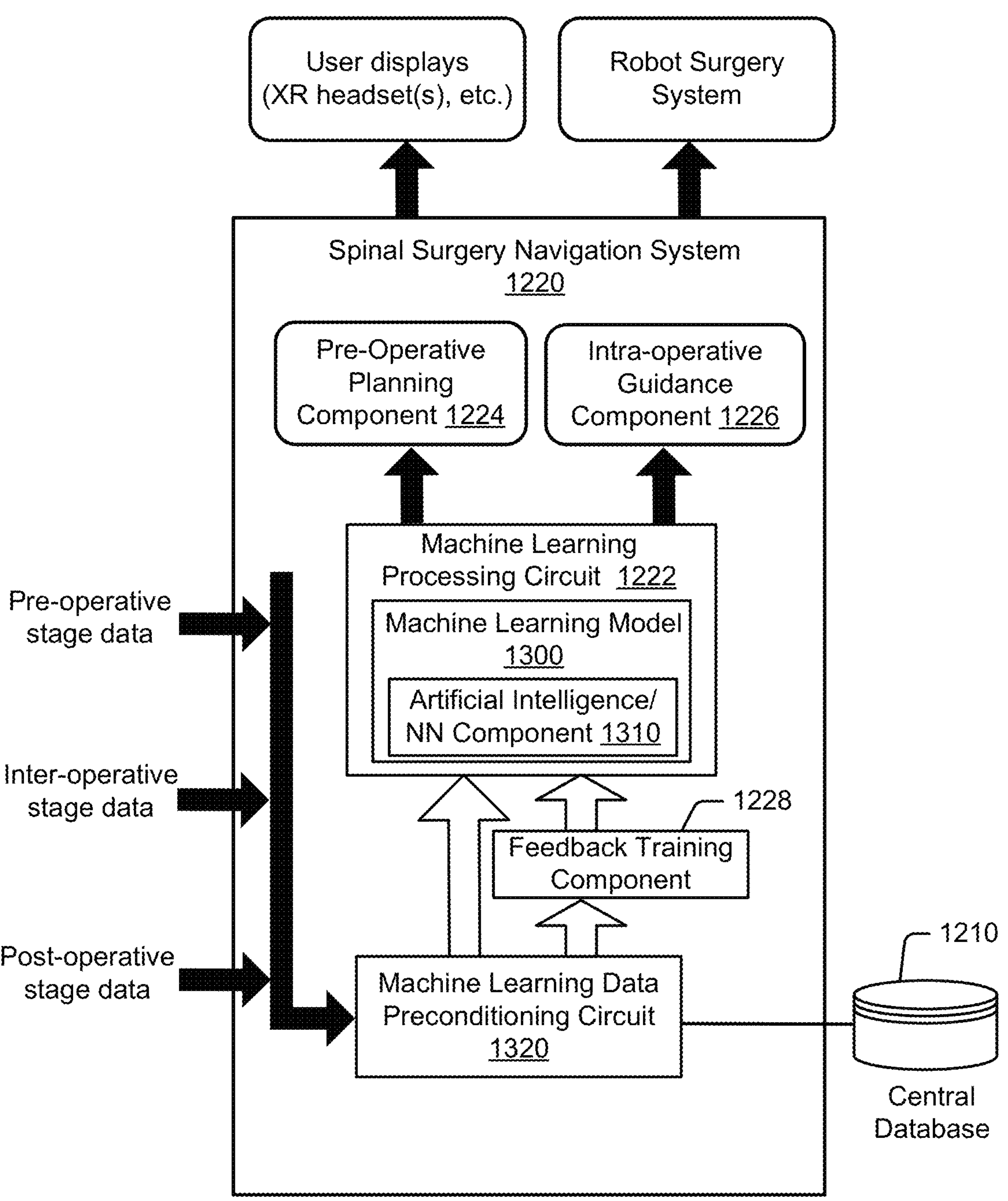
FIG. 2 illustrates a block diagram of the spinal surgery navigation system with associated data flows during the pre-operative, intra-operative, and post-operative stages, and shows surgical guidance being provided to user displays and to a robot surgery system in accordance with some embodiments.

FIG. 2 illustrates a block diagram of the spinal surgery navigation system 1220 with associated data flows during the pre-operative, intra-operative, and post-operative stages, and shows surgical guidance being provided to user displays and to a robot surgery system.

Referring to FIG. 2, the spinal surgery navigation system 1220 includes the feedback training component 1228, the pre-operative planning component 1224, and the intra-operative guidance component 1226. The spinal surgery navigation system 1220 also includes machine learning processing circuit 122 that includes machine learning model 1300, which may include an artificial intelligence and/or neural network component 1310 as explained in further detail below.

The spinal surgery navigation system 1220 contains processing circuitry that is operative to obtain intra-operative feedback data and/or post-operative feedback data regarding spinal surgery outcome for a plurality of patients. A feedback training component 1228 is operative to train the machine learning model 1300 based on the intra-operative feedback data and/or the post-operative feedback data. The intra-operative feedback data and/or post-operative feedback data may also be stored in the central database 1210.

Pre-operative patient data characterizing a spine of a defined-patient is obtained and may be preconditioned by a machine learning data preconditioning circuit 1320, e.g., weighted and/or filtered, before being processed through the machine learning model 1300 to generate a spinal surgery plan for the defined-patient. The spinal surgery plan may be provided to a display device during pre-operative planning. During surgery, the spinal surgery plan may be provided to XR headset(s) worn by a surgeon and other operating room personnel and/or provide to other display devices to provide real-time navigated guidance to personnel according to the spinal surgery plan. Alternatively or additionally, the spinal surgery plan can be converted into instructions that guide movement of a robot surgery system, as will be described in further detail below.

The operation of the spinal surgery navigation system 1220 to generate the spinal surgery plan may include to process the pre-operative patient data through the machine learning model to identify predicted improvements to key points captured in medical images of the spine of the defined-patient.

The operation of the spinal surgery navigation system 1220 to generate the spinal surgery plan may include to process the pre-operative patient data through the machine learning model 1300 to output data indicating a planned access trajectory to access a target location on the spine of the defined-patient and/or data indicating a planned approach trajectory for implanting an implant device at the target location on the spine of the defined-patient.

The operation of the spinal surgery navigation system 1220 to generate the spinal surgery plan may include to process the pre-operative patient data through the machine learning model to output data indicating at least one of: a planned implant location on the spine of the defined-patient; a planned size of an implant to be implanted on the spine of the defined-patient; and a planned interbody implant expansion parameter.

The operation of the spinal surgery navigation system 1220 to generate the spinal surgery plan may include to process the pre-operative patient data through the machine learning model to output data indicating planned amount of spine decompression to be surgically performed and/or indicating a planned amount of disc material of the spine to be surgically removed by a discectomy procedure.

The operation of the spinal surgery navigation system 1220 to generate the spinal surgery plan may include to process the pre-operative patient data through the machine learning model to output data indicating a planned curvature shape for a rod to be implanted during spinal fusion.

In some further embodiments, the spinal surgery navigation system 1220 can be further operative to obtain defined-patient intra-operative feedback data that includes at least one of: data characterizing deviation between an intra-operative spinal surgery process performed on the defined-patient and the spinal surgery plan for the defined-patient; data characterizing deviation between an intra-operative access trajectory used to access a target location on the spine of the defined-patient and an access trajectory indicated by the spinal surgery plan for the defined-patient; and data characterizing deviation between an intra-operative approach trajectory used to implant an implant device at the target location on the spine of the defined-patient and an approach trajectory indicated by the spinal surgery plan for the defined-patient. The feedback training component 1228 can be configured to train the machine learning model 1300 based on the defined-patient intra-operative feedback data.

In some further embodiments, the spinal surgery navigation system 1220 can be further operative to obtain defined-patient intra-operative feedback data that includes at least one of: data characterizing an intra-operative measurement of amount of spine decompression obtained during spinal surgery according to the spinal surgery plan on the defined-patient; data characterizing an intra-operative measurement of amount of soft tissue disruption during spinal surgery according to the spinal surgery plan on the defined-patient; and data characterizing an intra-operative measurement of amount of disc material of the spine surgically removed by a discectomy procedure according to the spinal surgery plan on the defined-patient. The feedback training component 1228 can be configured to train the machine learning model 1300 based on the defined-patient intra-operative feedback data.

In some further embodiments, the spinal surgery navigation system 1220 can be further operative to obtain defined-patient intra-operative feedback data that includes at least one of: data characterizing post-operative measurements of spine decompression captured in medical images of the spine of the defined-patient following spinal surgery; data characterizing post-operative measurements of spinal deformation captured in medical images of the spine of the defined-patient following spinal surgery; data characterizing post-operative measurements of amount of removed disc material of the spine captured in medical images of the spine of the defined-patient following the spinal surgery; and data characterizing post-operative measurements of amount of soft tissue disruption captured in medical images of the defined-patient following the spinal surgery. The feedback training component 1228 can be configured to train the machine learning model 1300 based on the defined-patient post-operative feedback data.

In some further embodiments, the spinal surgery navigation system 1220 can be further operative to obtain defined-patient post-operative feedback data that includes at least one of: data characterizing implant failure following spinal surgery on the defined-patient; data characterizing bone failure following spinal surgery on the defined-patient; data characterizing bone fusion following spinal surgery on the defined-patient; and data characterizing patient reported outcome measures following spinal surgery on the defined-patient. The feedback training component 1228 can be configured to train the machine learning model 1300 based on the defined-patient post-operative feedback data.

The machine learning model 1300 can include a neural network component 1310 that includes an input layer having input nodes, a sequence of hidden layers each having a plurality of combining nodes, and an output layer having output nodes. At least one processing circuit (e.g., data preconditioning circuit 1320) can be configured to provide different entries of the intra-operative feedback data and/or the post-operative feedback data to different ones of the input nodes of the neural network component 1310, and to generate the spinal surgery plan based on output of output nodes of the neural network component 1310.

The feedback training component 1228 may be configured to adapt weights and/or firing thresholds that are used by the combining nodes of the neural network component 1310 based on values of the intra-operative feedback data and/or the post-operative feedback data.

For example, during run-time mode and training mode, the interconnected structure of the neural network component 1310 between the input nodes of the input layer, the combining nodes of the hidden layers, and the output nodes of the output layer can cause the inputted values to simultaneously be processed to influence the generated output values that are used to generate the spinal surgery plan. Each of the input nodes in the input layer multiply the input characterization data value by a weight that is assigned to the input node to generate a weighted node value. When the weighted node value exceeds a firing threshold assigned to the input node, the input node then provides the weighted node value to the combining nodes of a first one of the sequence of the hidden layers. The input node does not output the weighted node value unless if the condition is satisfied where the weighted node value exceeds the assigned firing threshold.

Furthermore, the neural network component 1310 operates the combining nodes of the first one of the sequence of the hidden layers using weights that are assigned thereto to multiply and mathematically combine weighted node values provided by the input nodes to generate combined node values, and when the combined node value generated by one of the combining nodes exceeds a firing threshold assigned to the combining node to then provide the combined node value to the combining nodes of a next one of the sequence of the hidden layers. Furthermore, the neural network component 1310 operates the combining nodes of a last one of the sequence of hidden layers using weights that are assigned thereto to multiply and combine the combined node values provided by a plurality of combining nodes of a previous one of the sequence of hidden layers to generate combined node values, and when the combined node value generated by one of the combining nodes exceeds a firing threshold assigned to the combining node to then provide the combined node value to the output nodes of the output layer. Finally, the output nodes of the output layer is then operated to combine the combined node values from the last one of the sequences of hidden layers to generate the output values used for generating the spinal surgery plan.

A machine learning data preconditioning circuit 1320 may be provided that pre-processes the obtained data, such as by providing normalization and/or weighting of the various types of obtained data, which is then provided to machine learning processing circuit 1222 during a run-time phase or to the feedback training component 1228 during a training phase for use in training the machine learning model 1300. In some embodiments, the training is performed continuously or at least occasionally during run-time.

A pre-operative planning component 1224 contains pre-operative data from one of the distributed network computers characterizing a defined-patient, generates a spinal surgery plan for the defined-patient based on processing the pre-operative data through the machine learning model 1300, and provides the spinal surgery plan to a display device for review by a user.

Thus, as explained above, the training can include adapting rules of an AI algorithm, rules of one or more sets of decision operations, and/or weights and/or firing thresholds of nodes of a neural network mode, to drive one or more defined key performance surgical outcomes indicated by the pre-operative data and/or the intra-operative data toward one or more defined thresholds or other rule(s) being satisfied.

The machine learning model 1300 can be configured to process the pre-operative data to output the spinal surgery plan identifying an implant device, a pose for implantation of the implant device in the defined-patient, and a predicted post-operative performance metric for the defined-patient following the implantation of the implant device.

Figure 8:
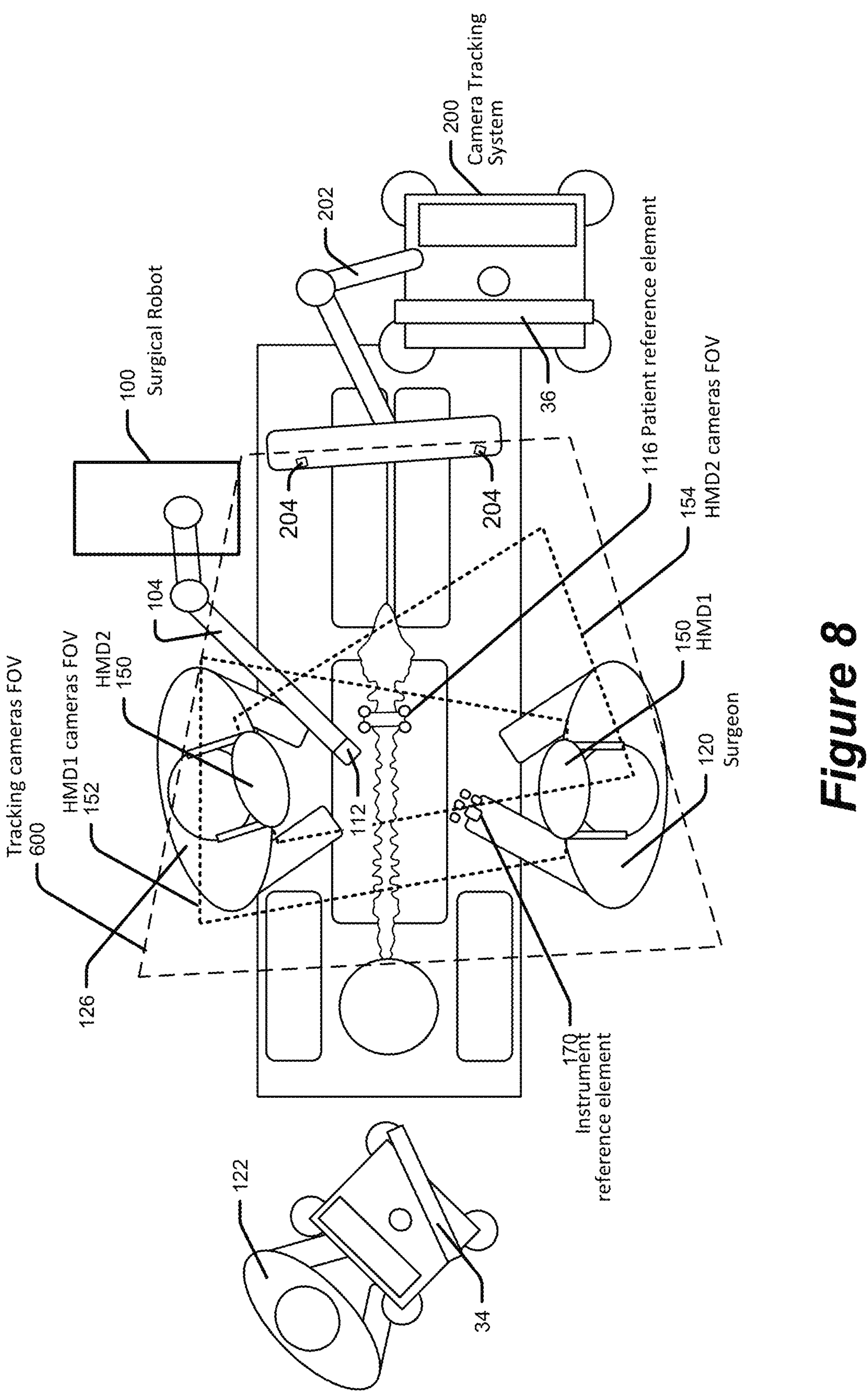

The machine learning model 1300 can be further configured to generate the spinal surgery plan with identification of planned access trajectory to access a target location on the spine of the defined-patient and/or data indicating a planned approach trajectory for implanting an implant device at the target location on the spine of the defined-patient. A pre-operative planning component 1224 may provide data of the spinal surgery plan to a computer platform 400 (e.g., FIG. 8) that allows review and modification of the plan by a surgeon. An intra-operative guidance component 1226 may provide navigation information according to the spinal surgery plan to one or more display devices for viewing by a surgeon and/or other operating room personnel, e.g., to see-through display device 438 in an extended reality (XR) headset 150 (FIG. 8) for viewing as an overlay on the defined-patient. The intra-operative guidance component 1226 may provide steering information to a robot controller of a surgical robot 100 (FIG. 8). The surgical robot 100 can include a robot base, a robot arm connected to the robot base and configured to guide movement of the surgical instrument, and at least one motor operatively connected to control movement of the robot arm relative to the robot base. The robot controller can control movement of the at least one motor based on the steering information to guide repositioning of the surgical instrument to become aligned with the target pose.

During surgery (i.e., the intra-operative stage) the spinal surgery navigation system 1220 can be configured to provide the surgical plan to a display device to assist a user (e.g., surgeon) during surgery. In some embodiments, a surgical system includes the spinal surgery navigation system 1220 as a sub-system for computer assisted navigation during surgery, a camera tracking sub-system 200 (FIG. 5), and a navigation controller 404 (FIG. 8). As explained above, the spinal surgery navigation system 1220 is configured to: obtain post-operative feedback data provided by distributed networked computers regarding surgical outcomes for a plurality of patients; train a machine learning model based on the post-operative feedback data; and obtain pre-operative data from one of the distributed network computers characterizing a defined-patient, generate a spinal surgery plan for the defined-patient based on processing the pre-operative data through the machine learning model.

The camera tracking sub-system 200 (FIG. 5) is configured to determine a pose of the spine of the defined-patient relative to a pose of a surgical instrument manipulated by an operator and/or a surgical robot. The navigation controller 404 (FIG. 8) is operative to obtain the spinal surgery plan from the spinal surgery navigation sub-system 1220, determine a target pose of the surgical instrument based on the spinal surgery plan indicating where a surgical procedure is to be performed on the spine of the defined-patient and based on the pose of the spine of the defined-patient, and generate steering information based on comparison of the target pose of the surgical instrument and the pose of the surgical instrument.

In some embodiments, the surgical system includes an XR headset 920 with at least one see-through display device 438 (FIG. 8). An XR headset controller 410 may partially reside in the computer platform 400 or in the XR headset 150, and is configured to generate a graphical representation of the steering information that is provided to the at least one see-through display device of the XR headset 920 to provide navigated guidance to the wearer according to the spinal surgery plan. For example, the navigation controller may be operative to generate a graphical representation of the steering information that is provided to XR headset controller 410 for display through the see-through display device 438 of the XR headset 150 to guide operator movement of the surgical instrument to become aligned with a target pose according to the spinal surgery plan.

To generate the spinal surgery plan and train the machine learning model 1222, data is need from multiple sources to establish a baseline machine learning model that is then trained over time to provide improved patent specific outcomes from the generated spinal surgery plans.

Figure 3:
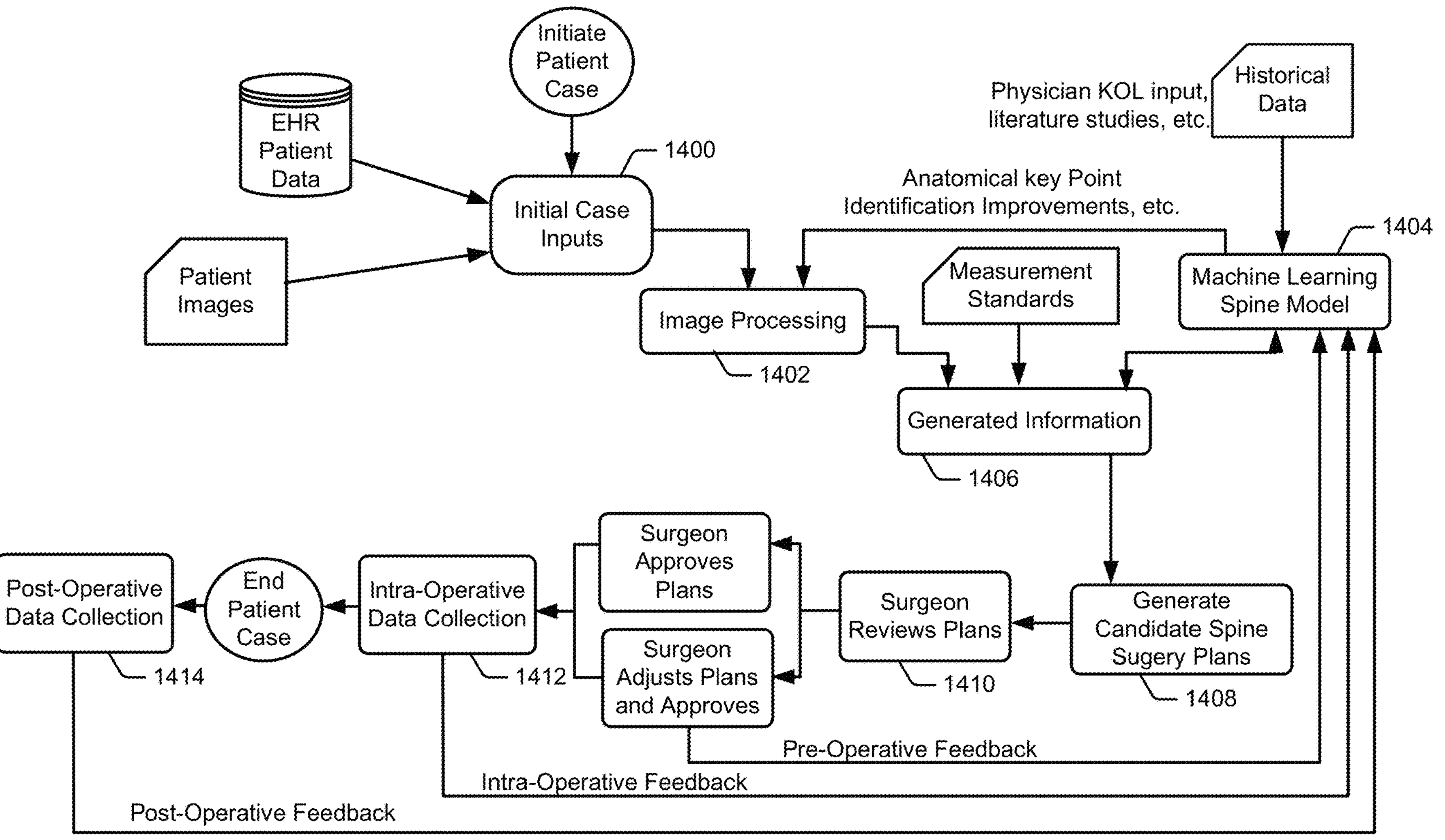
FIG. 3 illustrates an operational flowchart for generating a spinal surgery plan based on processing pre-operative patient data through a machine learning spine model, and for using intra-operative feedback data and/or post-operative feedback data to train the machine learning spine model in accordance with some embodiments.

FIG. 3 illustrates an operational flowchart for generating a spinal surgery plan based on processing pre-operative patient data through a machine learning spine model 1404, and for using intra-operative feedback data and/or post-operative feedback data to train the machine learning spine model 1404.

Referring to FIG. 3, responsive to initiation of a patient case, pre-operative data is provided as initial patient case inputs 1400. The pre-operative initial patient case inputs 1400 may be obtained from EHR patient data and/or patient images.

The electronic health record (EHR) patient data may include, without limitation, any one or more of:

1) date of birth, which may be used to select parameters for the machine learning spine model, e.g., adult or pediatric;
2) height;
3) weight/BMI;
4) gender;
5) ethnicity;
6) race;
7) bone Density, e.g., obtained from test results of Dual-Energy X-ray Absorptiometry (DEXA) scan (t-score and z-score), and/or CT scan (Hounsfield Scale);
8) menarchal status;
9) skeletal of maturity, e.g., Sander's score;
10) complete Blood Count (CBC);
11) blood Morphogenic Proteins (BMP);

12) coagulation Factors;
13) EKGs;
14) medication history, e.g., teriparatide status or other medications influencing bone density;
15) general medical history, e.g., nicotine status, substance abuse, medical conditions, known allergies, previous failed spinal surgeries, diabetes, rheumatoid arthritis, any degenerative diseases;
16) psychological evaluation section;
17) demographic characteristics;
18) activity characteristics—physical therapy status, activity level descriptor;
19) doctor's notes;
20) past spinal surgical procedures, e.g., fusions, spinal cord stimulator, non-surgical interventions, etc.;
21) current diagnoses, e.g., pathologies/location; radiculopathy, myelopathy; and
22) patient imaging scans.

Historical data can be provided to the machine learning spine model 1404 for training of the model 1404 and for use in generating machine learning-based outputs that may be used to perform the image processing 1402 and/or to determine the generated information 1406 and generate the candidate spine surgery plans 1408. The historical data may include, without limitation, physician Key Opinion Leader (KOL) data input and/or data from literature studies such as any one or more of:

1) spinal anatomical trends, e.g., size, shape, patterns;
2) spinal alignment parameters, e.g., accepted normative ranges;
3) spinal alignment measurement methodologies;
4) spinal stiffness matrix;
5) initial trained machine learning algorithms from pre-op and/or post-op patient images with known outcomes;
6) surgical intervention expertise; and
7) diagnosis criteria(s).

More specifically in the context of spinal surgery, the historical data may include any one or more of: spinal alignment target values; spinal anatomical trends; surgeon approach techniques; spine stiffness data; diagnosis criteria; and known correlations for best outcomes from surgical techniques.

The patient images may be obtained from imaging devices 420 (FIG. 8), such as a computed tomography C-arm image device and/or computed tomography O-arm imaging device, and/or may be obtained from image database(s). The patient images may be retrieved from the central database 1210 (FIG. 2) using a patient identifier.

Image processing 1402 of the patient images may be performed using the machine learning spine model 1404 which can be configured to generate synthetic CT image modality images of the patient's spine from MRI modality images of the patient's spine. Other image processing 1402 operations can include to generate synthetic CT image modality images from a plurality of fluoro shots, e.g., AP and lateral fluoro images.

Alternatively or additionally, the image processing may be performed using the machine learning spine model 1404 which can be configured to identify anatomical key points and datums, determine segmentation, colorization, and/or identify patient spinal anatomy, e.g., bone and soft tissue structures. Sizes of the images anatomical structures can be determined based on segment locations and overall structure size. Spine stiffness and bone density may be estimated based on the image processing and the other initial case inputs. Stenosis of the spine, central and/or lateral recess, can be characterized based on processing initial case inputs 1400 through the machine learning spine model 1404. Foraminal height(s), disc height(s) (e.g., anterior or posterior, medial or lateral), CSF fluid around spinal cord and nerve roots, current global alignment parameters, can be characterized based on processing initial case inputs 1400 through the machine learning spine model 1404 and using measurement standards.

Generated information 1406 from the initial case inputs 1400, image processing 1402, and measurement standards, and historical data, along with output of the machine learning spine model 1404, can include, but is not limited to, any one or more of the following:

1) medical diagnoses of the patient, such as inputs from surgeon and/or output from the machine learning spine model 1404;
2) one or more candidate spine surgery plans;
3) predication of likelihood of complications from surgery performed according to the one or more candidate spine surgery plans, which may be based on inputs from surgeon and/or output from the machine learning spine model 1404;
4) predicted ideal global alignment parameters and level of intervention needed;
5) approach options with predicted outcomes displayed as function of:
   i. direct versus indirect, e.g., when is indirect decompression a sufficient intervention;
   ii. indirect decompression options and/or scenarios;
   iii. implant auto-plans, e.g., interbody size, location, lordosis or expansion parameters, fixation implant size and/or location, rod size and/or diameter and/or material, collision avoidance, instrument depth control set points;
   iv. deformity solution(s);
   v. auto-plan of rod curvature to align with posterior instrumentation and ability to translate that plan to an automatic rod bender instrument;
   vi. foraminal and/or spinal canal height restoration prediction; and
   vii. alignment correction.

The surgeon reviews 1410 the one or more candidate spine surgery plans and may approve (select) one of the candidate spine surgery plans or adjust one of the candidate spine surgery plans for approval. The approved candidate spine surgery plan is provided as pre-operative feedback to train the machine learning spine model 1404.

The approved candidate spine surgery plan can be provided to the intra-operative guidance component 1226 (FIG. 2) where it can be used to generate navigation information to guide an surgeon or other personnel through a spinal surgery procedure according to the approved candidate spine surgery plan. Alternatively or additionally, the intra-operative guidance component 1226 may provide the approved candidate spine surgery plan as steering information to the robot controller to control movement of the robot arm according to the approved candidate spine surgery plan.

Intra-operative data is collected 1412 and is provided as intra-operative feedback for training the machine learning spine model 1404. The Intra-operative data can include, but is not limited to, any one or more of the following:

1) finalized implant plans, e.g., spine level, type (VBR, disc replacement, interbody spacer), size, expansion parameters, location data in reference to anatomical key points and implant position;
2) finalized access approach, e.g., anterior cervical discectomy and fusion (ACDF), Posterior Cervical, lateral lumbar interbody fusion (LLIF), anterior lumbar interbody fusion (ALIF), posterior lumbar interbody fusion (PLIF), transforaminal lumbar interbody fusion (TLIF), etc.;

3) Port sizes used, such as bi-portal or uniportal sizes;
4) intra-operative vertebral body and instrumentation navigation and location history tracking, which may include any one or more of:
   i. comparison of tracked vertebral body alignment measures;
   ii. degree of soft tissue disruption, e.g., based on approach, access style, level of decompression;
   iii. degree of direct decompression or resection;
   iv. port size used, which may include total working region versus actual bone removed within a working region;
   v. implant cannula placement;
   vi. degree of discectomy tissue removed;
   vii. force measurements, e.g., from corrective loads, implant loads; and
   viii. stiffness sensors;
5) smart driver information feedback on torque and expansion;
6) smart implant information feedback on load and/or force distributions across implant, position;
7) neuromonitoring data;
8) ultrasonics data;
9) biologics used;
10) robot surgery system operation data logs;
11) surgical time, e.g., access, decompressions, discectomy, interbody placement, fixation placement, overall, etc;
12) re-registration scans; and
13) updates to measured parameters and/or plan based on new registration.

After the patient surgical procedure has been completed (end patient case), post-operative data is collected 1414 and is provided as post-operative feedback for training the machine learning spine model 1404. The post-operative data can include, but is not limited to, any one or more of the following:

1) Patient Reported Outcomes (PROs);
2) post-operative patient imaging scans;
3) deviation of spinal surgery plan versus actual placement of implants, which may be determined through pre-operative patient imaging scans with implant plans compared to post-operative patient imaging scans;
4) expected lordosis and/or correction compared to actual, e.g., which can be used to establish expected accuracies and outcomes and which indicate height restoration such as disc height, foraminal height (left vs. right), etc.;
5) implant failures;
6) bone failures;
7) fusion rates;
8) ASD reporting (levels affected in relation to surgical intervention, evidence of facet violation (if any));
9) Patient Reported Outcome Measures (PROMs); and
10) short-term and long-term patient medical data measurements, and observed changes over time in the data measurements.

Through machine learning, anatomical standards, pre/intra/post-operative data collection, and known patient outcomes), the machine learning spine model 1404 can be trained and eventually be predictive enough to determine or suggest possible diagnoses, determine ideal access approach (es), degree of decompression needed (indirect and/or direct), required interbody size/placement, custom interbody expansion set points (height and lordosis), and fixation type/size/placement that would be required for the most ideal spinal correction and patient outcomes. The need for this type of capability ranges from complex spinal deformity cases to single level degenerative spinal cases, like in the ILIF procedure, and could be beneficial for every type of spinal correction surgery including vertebral body replacements, and disc replacements.

Improvement of pre-operative spinal surgery plans can be provided by analysis of intra-operative and post-operative data. Use of the pre-operative feedback, intra-operative feedback, and post-operative feedback to train the machine learning spine model 1404 can enable more accurate prediction of patient specific outcomes through a candidate spine surgery plan and the generation of the spine surgery plan can be optimized to provide more optimal patient specific outcomes. The spine surgery plan generated using the trained machine learning spine model 1404 can use more optimally selected procedure types, implant types, access types, levels (amount) of decompression needed (indirect versus direct, and amount (degrees) of either), etc. The operations can be performed using XR imaging, endoscopic camera imaging, and/or ultrasonic imaging. The spinal surgery plan(s) can be generated based on learned surgeon preference(s) and/or learned standard best practices.

Various embodiments of the present disclosure may use post-operatively obtained data for correlation with a surgical plan and execution in order to:

- Provide guidance information that enables a user to understand performance metrics that are predicted to be obtained through the selection of available surgical plan variables; and
- Provide machine learning, such may include artificial intelligence (AI), assistance to a surgeon when performing patient-specific planning:
  - Defining target deformity correction(s) and/or joint line(s) through the planned surgical procedure; and/or
  - Defining selection of a best implant for use with the patient.

Figure 4:
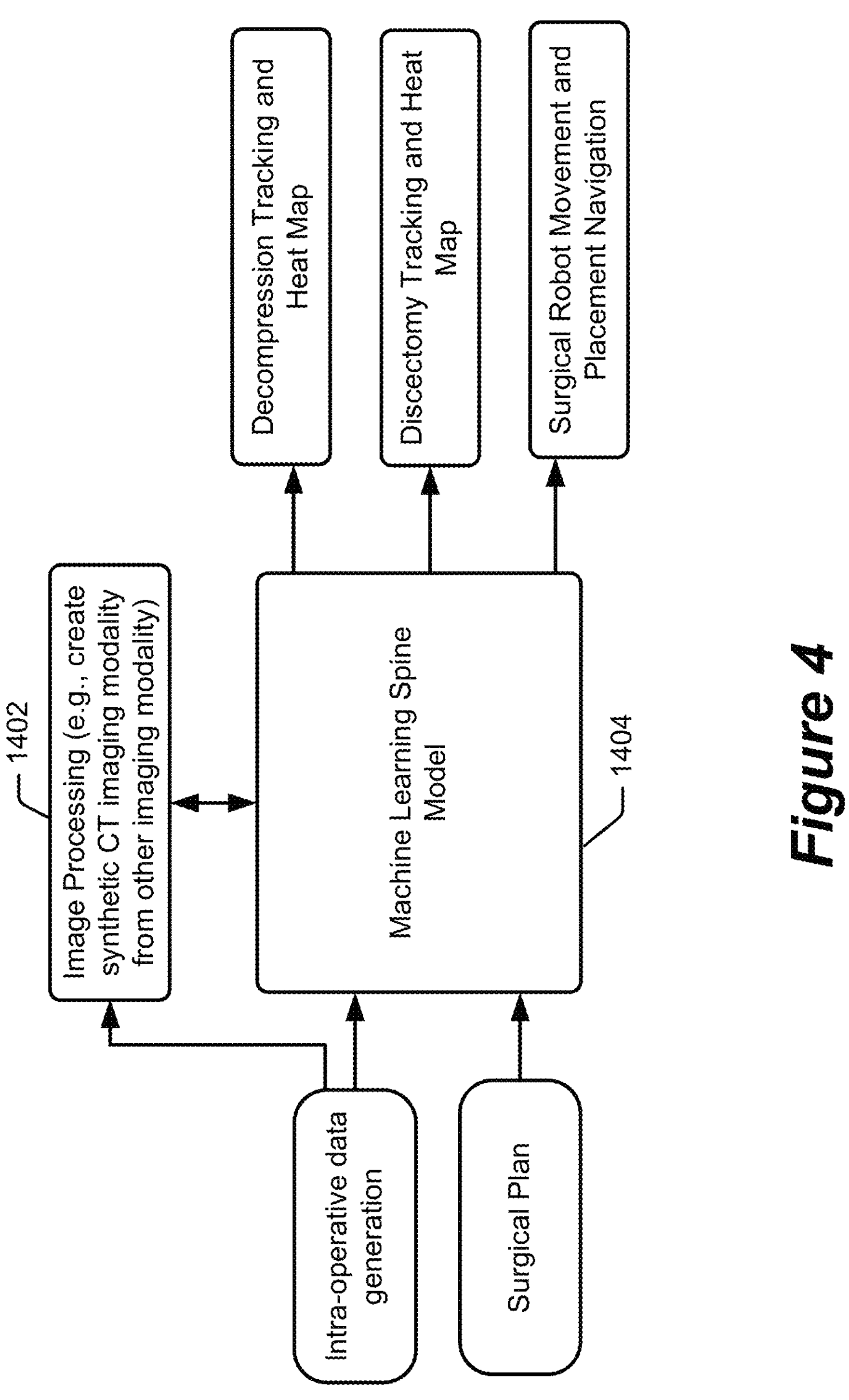
FIG. 4 illustrates a further operational flowchart for generating a spinal surgery plan in accordance with some embodiments.

FIG. 4 illustrates a further operational flowchart for generating a spinal surgery plan in accordance with some embodiments.

Referring to FIG. 4, as explained above, the image processing 1402 of the patient images may use the machine learning spine model 1404 to generate synthetic CT image modality images of the patient from MRI modality images of the patient, from a plurality of fluoro shots of the patient, e.g., AP and lateral fluoro images, and/or from images and/or data obtained through other imaging modalities. The machine learning spine model 1404 may be configured to process intra-operative data and the spinal surgery plan to generate a decompression tracking and heat map, which may include a pre-operative heat map and/or an intra-operative heat map.

The pre-operative heat map may provide visualization of where bony, and ligamentous anatomy should be removed for best outcomes pursuant to the spinal surgery plan generated based on surgeon input and output of the machine learning spine model 1404. The intra-operative heat map may provide visualization of the plan versus real-time feedback indicating the actual bone or ligament removal through use of tracked instrumentation and tool path history, e.g., from the camera tracking system 200 (FIG. 8). The pre-operative heat map and intra-operative heat map allow for integration of controlled aspects with power-controlled instrumentation, such as CNC controlled instrumentation.

FIG. 4 further illustrates that the machine learning spine model 1404 may be configured to process intra-operative data and the spinal surgery plan to generate a discectomy tracking and heat map which may include a pre-operative heat map and an intra-operative heat map. The pre-operative heat map may provide visualization of where disc tissue material should be removed for best outcomes, based on available discectomy instrumentation reach, interbody placement ability, etc., pursuant to the spinal surgery plan generated based on surgeon input and output of the machine learning spine model 1404. The intra-operative heat map may provide visualization of the plan versus real-time feedback indicating the actual disc material removal through use of tracked instrumentation and tool path history, e.g., from the camera tracking system 200 (FIG. 8). The pre-operative heat map and intra-operative heat map allow for integration of controlled aspects with power-controlled instrumentation, such as CNC controlled instrumentation.

FIG. 4 further illustrates that the machine learning spine model 1404 may be configured to process intra-operative data and the spinal surgery plan to generate instructions for surgical robot movement and/or robot placement navigation. The operations may identify a candidate position for robot placement and overall operating room setup layout of operating room equipment, access approach, pre-operative plan or trajectories for optimum robot arm reachability, and end effector attachment trajectories, e.g., IFIF guide bar. The robot placement prediction may provide an ability for a user to virtually move the robot and re-run a reachability check.

As explained above, one of the key aspects of the trained spine models based on the above inputs, is drawing correlations from intra-operative hard and soft tissue removal and how that relates to overall patient outcomes. An explanation is now provided for how decompression and discectomy instrument tracking data and patient reported outcomes can be used to develop better pre-operative plans.

Decompression Decision Making

There remains debate among surgeons on whether direct decompression or indirect decompression, as well as what level of each, is the higher contributor to obtaining better patient outcomes for interbody fusion cases in improving myelopathy and radiculopathy symptoms. Myelopathy refers to symptoms from spinal cord compression, while radiculopathy refers to symptoms due to compression of the nerve roots. These symptoms include pain, loss of movement, and loss of sensation to parts of the body.

Direct decompression generally is referred to as the process of directly removing the physical structure (e.g. bone, ligamentum flavum, herniated disc) that is compressing the nerves or spinal canal as well as relieving stenosis. Indirect decompression refers to decompressing the impinged area by a process of distracting the space with interbody in the disc space, and using posterior fixation for realignment without physically resecting the compressing bone, tissue, or stenosis.

In lumbar fusion cases, surgeons typically rely on a combination of the two, with varying higher consideration of one over the other. This remains due to surgeon experience, training, and lack of literature definitively supporting one over the other.

Various embodiments of the present disclosure are directed to using machine learning based on a predetermined list of pre-operative, intra-operative, and post-operative data points to identify possible correlations between type of decompression, and amount of decompression, and positive patient reported outcomes, and other combinations thereof. Auto segmentation and key point identification or plane identification of the patient scan provides the ability to accurately model the patient's anatomy, and when paired with intra-operative tool history tracking (e.g. burrs, Kerrison, etc.), develops a heat map of tissue removal. This heat map depicts the amount of direct decompression performed, and anatomical location of the decompression. Intra-operative data collection also includes type of interbody and size used, interbody position, and expansion parameters relating to indirect decompression variables.

As the amount of collected data increases between different patients, and surgeons performing varying decompressions, data mining algorithms can pull out the correlations between the parameters; including decompression techniques (amount of direct decompression (port size, area removed in and around port, etc.), location of direct decompression paired to the anatomy, interbody size/position and expansion optimization, etc.) for best patient reported outcomes. Additionally, measuring the speed and/or pressure of surgeon freehanded navigated instrumentation (i.e. burrs) linked to anatomical location establishes the basis for CNC controlled instrumentation.

Figure 5:
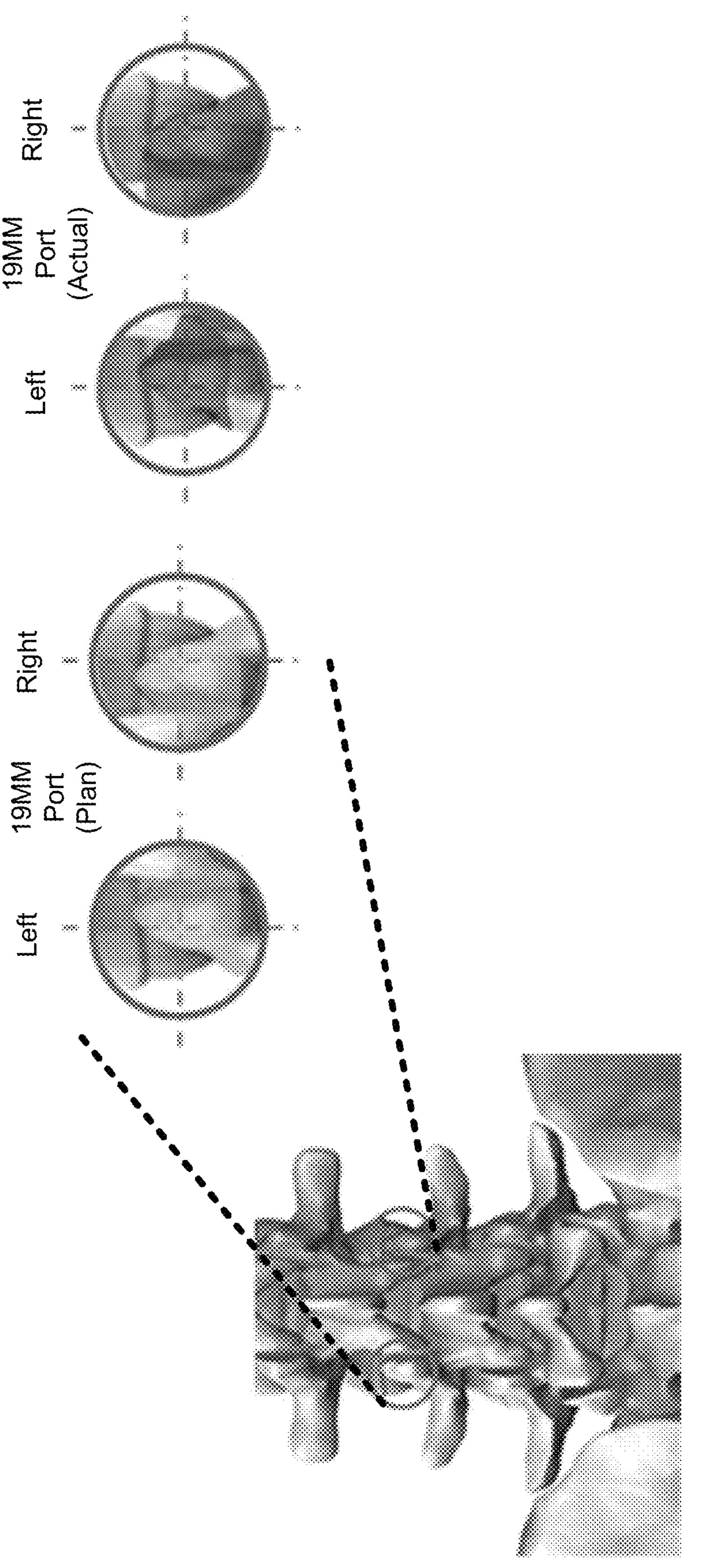
FIG. 5 illustrates how port size and planned direct decompression pathway are compared to actual direct decompression performed or bone removed in accordance with some embodiment.

As the data set grows larger, the patterns and possible cause-effect relationships can be used to train and/or update the planning algorithm (e.g., including the machine learning spine model 1404) to generate the auto-populated pre-operative surgical plan. For example, FIG. 5 depicts how port size (19 mm port) and planned direct decompression pathway are compared to actual direct decompression performed or bone removed. Port size is the total initial available working region where decompression could be contained within that region, or intra-operatively extended beyond that region if ports are manually adjusted along any degree of freedom. The direct decompression plan can be compared to the actual decompression performed intra-operatively and auto-plans can optimize for surgeon specific tendencies, and techniques determined to deliver improved patient outcomes though machine learning by the machine learning spine model 1404.

Stages of Direct Decompression Workflows—

In some embodiments, workflows for stages of direct decompression can include use of a pre-operative heat map and an intra-operative heat map.

The pre-operative heat can provide visualization of where bony, and ligamentous anatomy should be removed for best outcomes, based on outputs of the machine learning model (AI-assisted) for auto-populated plans and surgeon input. The pre-operative heat may be provided as an overlay view on patient images.

The intra-operative heat map can provide visualization of plan versus actual bone and/or ligament removal through tracked instrumentation and tool path history. The plan versus action data can include: tracked articulation; 2D and/or 3D visualization of bone removal in colorization for plan versus actual, as well as live 3D model displaying resected bone based on current tool and path; and allow for integration with power-controlled instrumentation, and CNC controlled instrumentation with active robot for go-no go zones based on plan.

Ultimately, between various patients, direct decompression plan and actual direct decompression can be compared with other post-operative metrics previously listed such as pain scales, and height restoration (disc and foramen, left vs right) collected over a repetition of both short-term and long-term post-operative data and reported outcomes. This, in addition to the indirect decompression metrics such as discectomy, interbody size/placement/expansion parameters (lordotic versus parallel) can also be compared to compile a bigger picture of cause and effect of decompression techniques (indirect and direct) to the best patient outcomes.

Discectomy Decision Making—

In some embodiments, tool history tracking is combined with data mining algorithms (e.g., as part of a machine learning model) to draw positive correlations to good patient outcomes, and is applied to the discectomy portion of interbody fusion procedures. Discectomy is the removal of the intervertebral disc in order to prepare the space for interbody placement, create an optimal environment for fusion, and to remove disc material directly impinging on neural elements. Current surgeon workflows for discectomy differ greatly based on varying instrumentation, extent of tissue removed, and degree of endplate prep. These variables are linked, but not limited to, surgeon approach and biomaterials being used.

Figure 6:
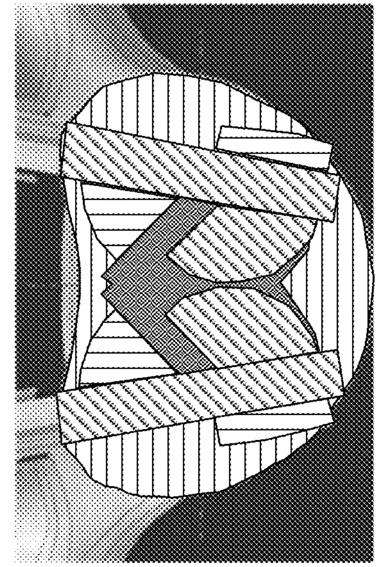
FIG. 6 illustrates heat maps that depict the amount of disc material removed, the anatomical location of the discectomy, and comparison of discectomy versus interbody planned placement, in accordance with some embodiments.
Figure 6:
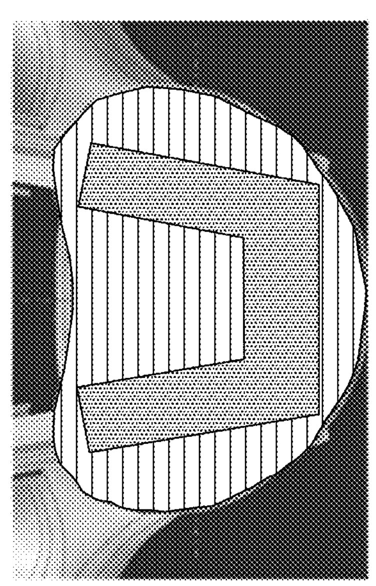
Figure 6:
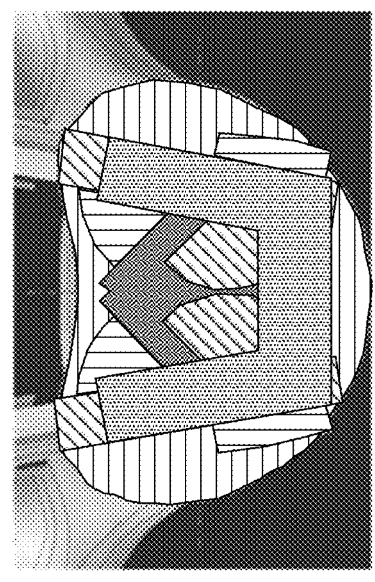
Figure 7:
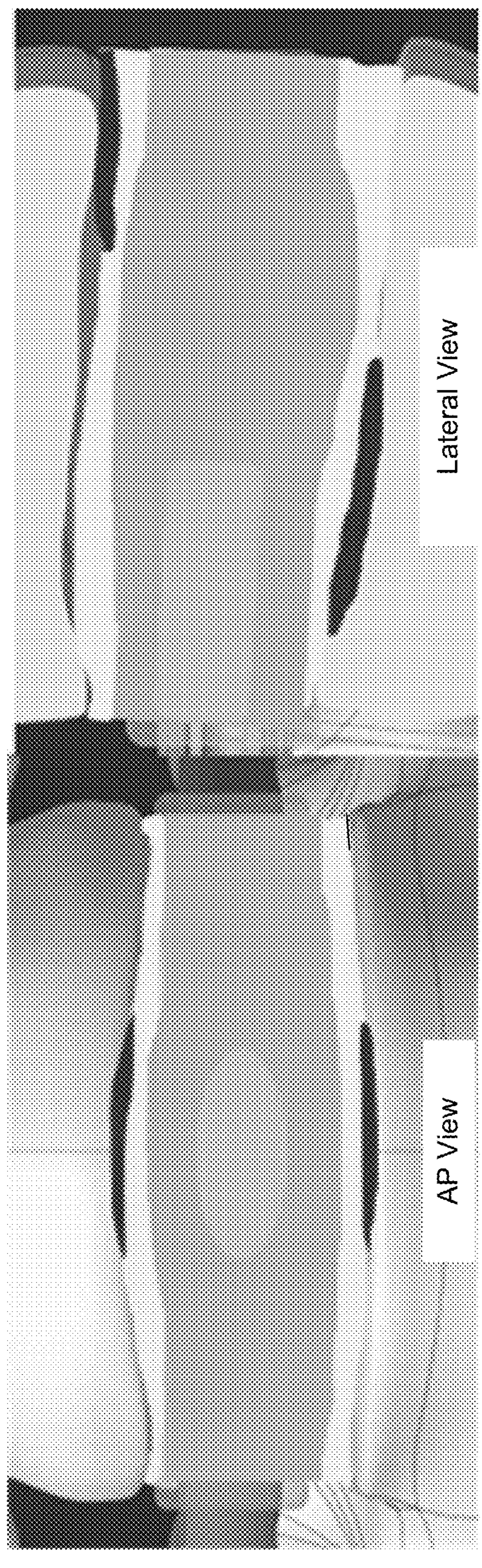
FIG. 7 illustrates central soft disc tissue removal versus superior or inferior endplate preparedness in accordance with some embodiments.

In accordance with some embodiments, data collection, auto-segmentation and key point/plane identification of the patient scan is used to accurately model the patient's anatomy, and may be paired with intra-operative tool history tracking during discectomy (e.g. pituitaries, curettes, brushes, etc.), to develop a heat map of disc tissue removal as depicted in FIG. 6 and FIG. 7. FIG. 6 illustrates heat maps that depict the amount of disc material removed, the anatomical location of the discectomy (disc space quadrants, central disc versus endplates), and comparison of discectomy versus interbody planned placement. FIG. 7 illustrates central soft disc tissue removal versus superior or inferior endplate preparedness.

Operations for intra-operative data collection can include recording the type of disc material removed based on tool location (tracked tool location) in the disc space between the annulus, nucleus, and cartilaginous endplate material. The following are some of the variables that the algorithm (e.g., part of a machine learning model) could draw correlations about with this data that may include any one or more of:

1) Accurate interbody placement to plan versus amount of actual tissue removed;
2) Fusion rates versus amount and type/location of tissue removed; and
3) "Effectiveness" and Completeness to plan Stages of Discectomy Workflows One stage of a discectomy workflow can be use of the machine learning model to generate a pre-operative heat map that provides visualization of any one or more of: where disc tissue material should be removed for best outcomes; available discectomy instrumentation reach; and/or interbody placement pursuant to auto-populated plans from the machine learning model. The visualization can be displayed as colorized image overlays on a patient scan. The pre-operative heat map may include surgeon provided input.

Another stage of the discectomy workflow can be further use of the machine learning model to generate an intra-operative heat map that provides visualization of the surgical plan versus intra-operative observations and measurements, which may include measurement of actual disc material removed through tracked instrumentation and tool path history. The intra-operative heat map may include any one or more of: tracked articulation; 2D and/or 3D visualization of progress of disc tissue removal in colorization for the surgical plan versus actual, as well as live 3D model of disc space displaying discectomy based on tool and path; and/or progress of soft tissue removal displayed as progressive change in colorization, with multiple passes in the same region building up to a finalized "cleared" area as opposed to bony removal that requires a singular tool pass to remove completely. The workflow may include integration with power-controlled instrumentation and CNC controlled instrumentation with active control of a surgical robot. The visualization may be provided to a see-through display screen of an XR headset to be displayed as an overlay on the patient's anatomy and/or displayed at locations(s) which may be anchored elsewhere in the operating room.

Figure 9:
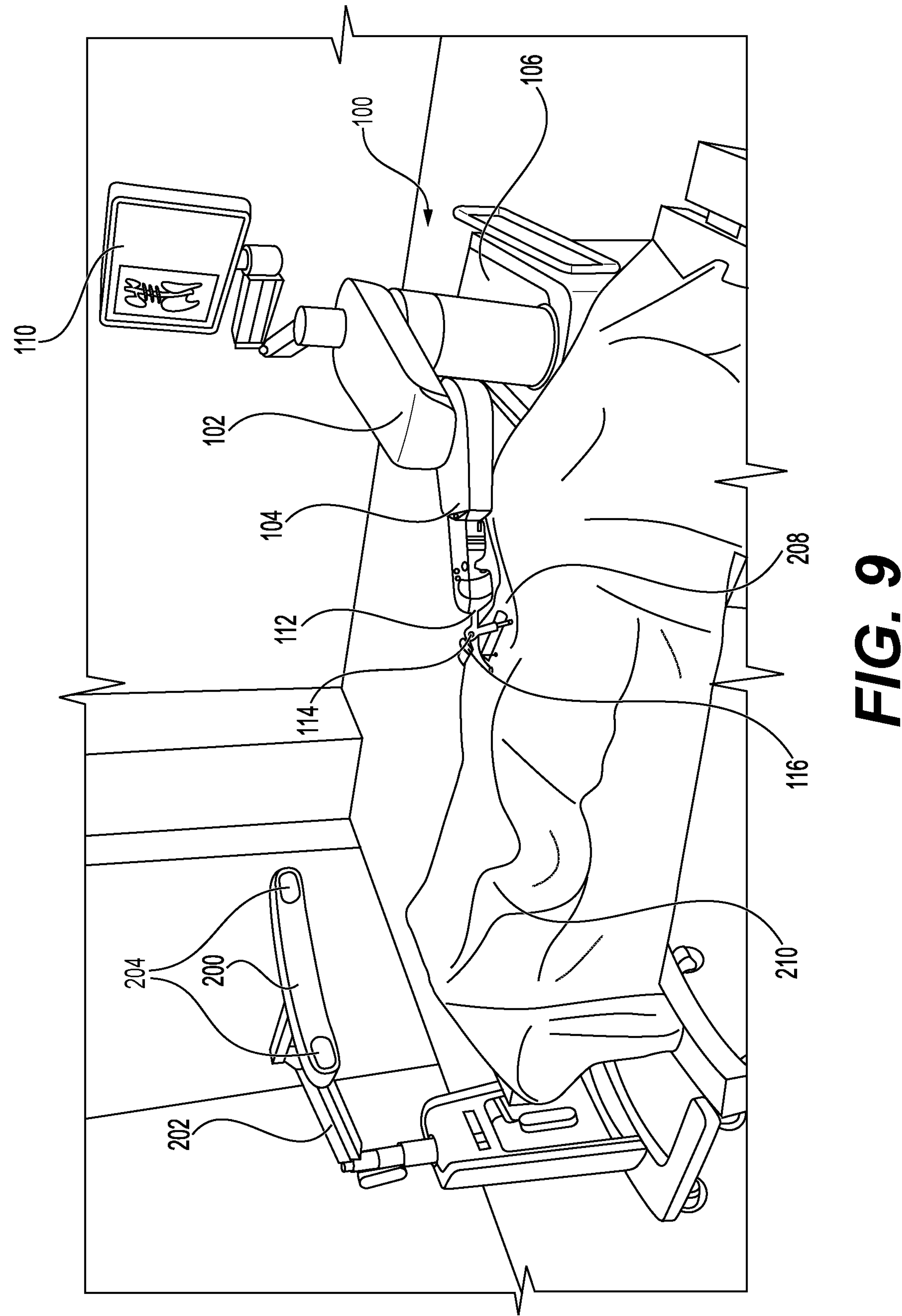
FIG. 9 illustrates the camera tracking system and the surgical robot positioned relative to a patient according to some embodiments.
Figure 10:
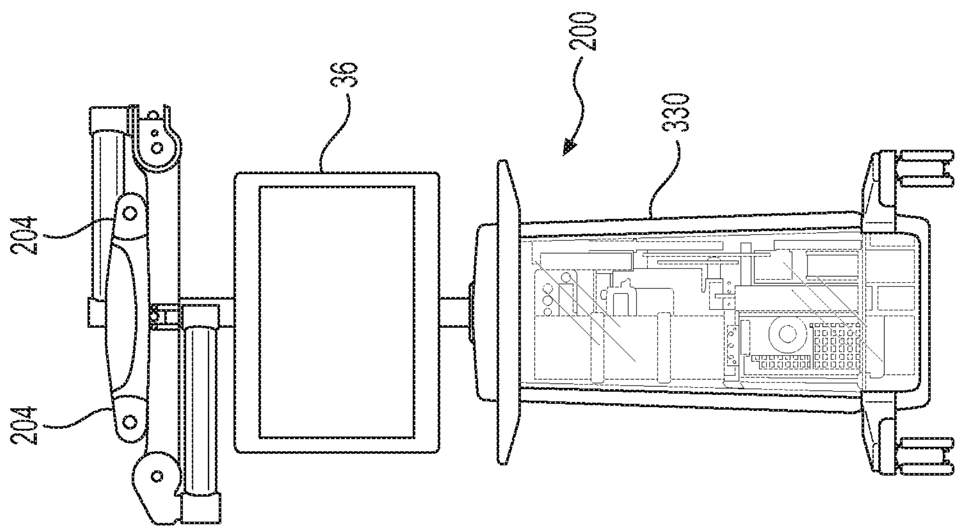
FIG. 10 further illustrates the camera tracking system and the surgical robot configured according to some embodiments.
Figure 10:
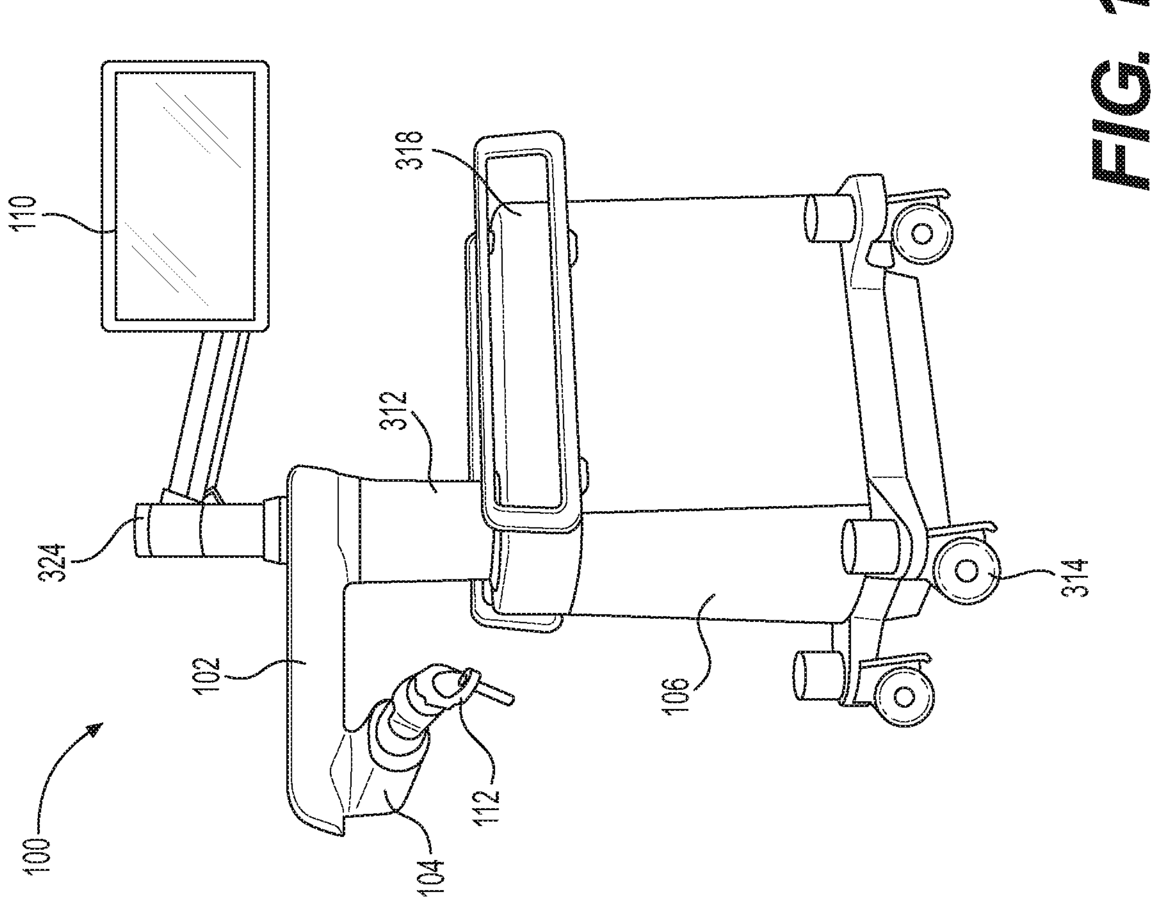
Figure 11:
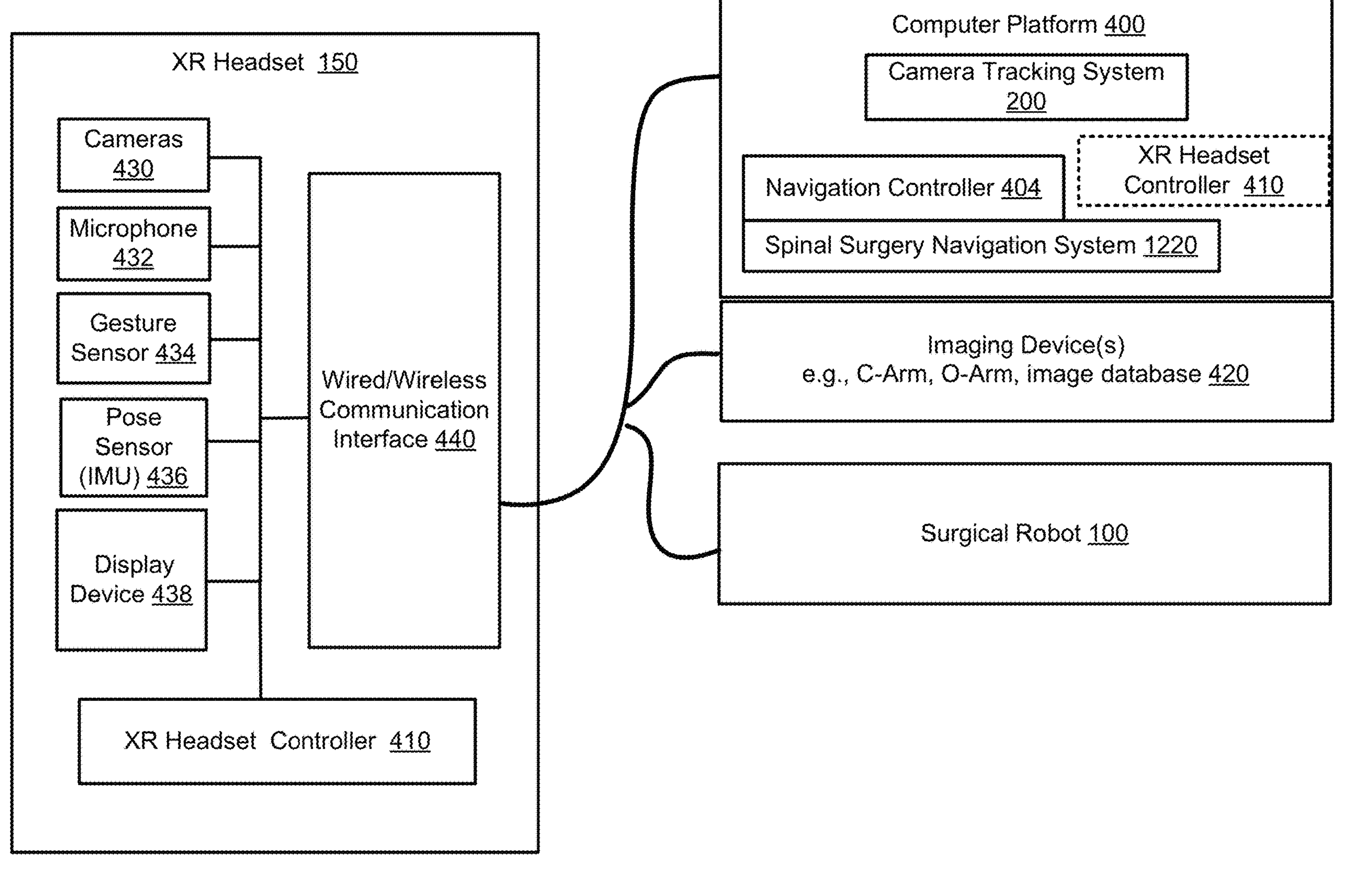
FIG. 11 illustrates a block diagram of a surgical system that includes an extended reality headset, a computer platform, imaging devices, and a surgical robot which are configured to operate according to some embodiments.

FIG. 8 is an overhead view of a surgical system arranged during a surgical procedure in a surgical room. The system includes a camera tracking system 200 for computer assisted navigation during surgery and may further include a surgical robot 100 for robotic assistance according to some embodiments. FIG. 9 illustrates the camera tracking system 200 and the surgical robot 100 positioned relative to a patient according to some embodiments. FIG. 10 further illustrates the camera tracking system 200 and the surgical robot 100 configured according to some embodiments. FIG. 11 illustrates a block diagram of a surgical system that includes an extended reality (XR) headset 150, a computer platform 400, imaging devices 420, and the surgical robot 100 which are configured to operate according to some embodiments.

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset can referred to as an AR headset or a VR headset.

Referring to FIGS. 8 through 11, the surgical robot 100 may include, for example, one or more robot arms 104, a display 110, an end-effector 112, for example, including a guide tube 114, and an end effector reference element which can include one or more tracking fiducials. A patient reference element 116 (DRB) has a plurality of tracking fiducials and is secured directly to the patient 210 (e.g., to a bone of the patient). A reference element 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual fiducial and pose of an array of fiducials of a reference element.

As used herein, the term "pose" refers to the location (e.g., along 3 orthogonal axes) and/or the rotation angle (e.g., about the 3 orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking fiducials for single fiducials (e.g., surveillance fiducial) and reference elements which can be formed on or attached to the patient 210 (e.g., patient reference element, DRB, etc.), end effector 112 (e.g., end effector reference element), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance fiducial and poses of reference elements within the XR camera headset field-of-views (FOVs) 152 and 154, respectively. Accordingly, as illustrated in FIG. 8, the location of the surveillance fiducial and the poses of reference elements on various objects can be tracked while in the FOVs 152 and 154 of the XR headsets 150 and/or a FOV 600 of the tracking cameras 204.

FIGS. 8 and 9 illustrate a potential configuration for the placement of the camera tracking system 200 and the surgical robot 100 in an operating room environment. Computer assisted navigated surgery can be provided by the camera tracking system controlling the XR headsets 150 and/or other displays 34, 36, and 110 to display surgical procedure navigation information. The surgical robot 100 is optional during computer assisted navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), imaging devices 420 (FIG. 11), and remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference element 116 (DRB) is generally rigidly attached to the patient with stable pitch and roll relative to gravity. This local rigid patient reference 116 can serve as a common reference for reference frames relative to other tracked elements, such as a reference element on the end effector 112, instrument reference element 170, and reference elements on the XR headsets 150.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 includes a guide tube 114, which is configured to receive and orient a surgical instrument, tool, or implant used to perform a surgical procedure on the patient 210. In some other embodiments, the end-effector 112 includes a passive structure guiding a saw blade (e.g., sagittal saw) along a defined cutting plate.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end-effector 112 (e.g., end-effector element 114 in FIG. 9), and/or a surgical instrument (e.g., instrument element 170) to enable tracking of poses in a defined coordinate system, e.g., such as in 6 DOF along 3 orthogonal axes and rotation about the axes. The reference elements enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 10 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 11 illustrates a block diagram of a surgical system that includes an XR headset 150, a computer platform 400, imaging devices 420, and a surgical robot 100 which are configured to operate according to some embodiments. The computer platform 400 may include the spinal surgery navigation system 1220 containing processing circuitry configured to operate according to one or more of the embodiments disclosed herein.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100. The navigation information may be displayed through the display device 438 of the XR headset 150 and/or another display device to indicate where the surgical tool and/or the end effector of the surgical robot 100 should be moved to perform a surgical procedure according to a defined surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

Navigated surgery using intra-operative tactile sensing based machine learning:

Further embodiments of the present disclosure are now explained which are directed to improving surgery outcomes through use of one or more sensor circuits which provide intra-operative tactile sensing of one or more characteristics of a tool which is contacting a location on patient anatomy within a surgical site. The intra-operative tactile sensing data is processed through a machine learning model to generate intra-operative navigated guidance data. The intra-operative navigated guidance data is provided to a display device and/or to a surgical robot to control movement of the tool.

As will be explained below, some embodiments are directed to configuring the surgery navigation system to operate to distinguish between biological components of the anatomy at a surgical site, such as where the tool or probe contacts bone versus soft tissue of the patient anatomy. The surgery navigation system may operate to generate plan progress information characterizing what portion of a region of a patient anatomy has been removed according to a surgical plan. The surgery navigation system may control movement of the tool by a robot arm of the surgical robot based on the plan progress information to direct the tool toward a remaining portion of the region of the patient anatomy to be removed according to the surgical plan. Alternatively or additionally, the surgery navigation system may control a display device based on the plan progress information to display a graphical indication of a remaining portion of the region of the patient anatomy to be removed according to the surgical plan.

For example, the surgery navigation system may operate to determine completed locations within an intradiscal space between interior and superior vertebral bodies where anatomical material has been removed according to a surgical plan, and control movement of the tool by an arm of a surgical robot to direct the tool toward a remaining portion of the anatomical material to be removed according to the surgical plan. Alternatively or additionally, the surgery navigation system may operate to display a graphical indication of where anatomical material has been removed from the intradiscal space and where anatomical material remains to be removed from the intradiscal space according to the surgical plan.

Some other embodiments are directed to training the machine learning model of the surgery navigation system based on collected intra-operative tactile sensing data and collected post-operative data.

Figure 12:
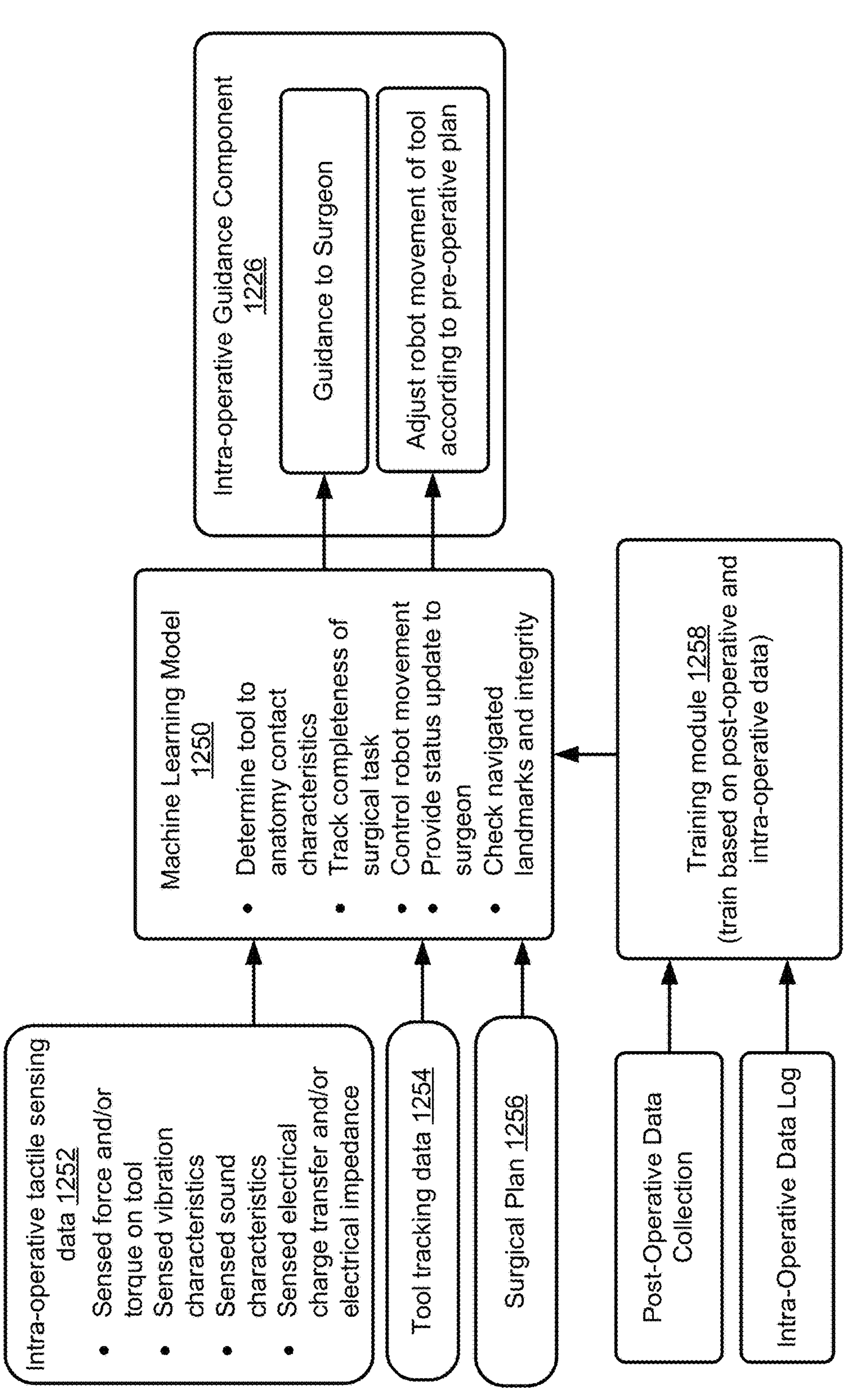
FIG. 12 illustrates a block diagram of a surgery navigation system showing intra-operative tactile sensing data and other data inputs to a machine learning model which outputs intra-operative navigated guidance data for computer assisted navigation during surgery according to some embodiments.

FIG. 12 illustrates a block diagram of a surgery navigation system showing intra-operative tactile sensing data 1252 and other data inputs to a machine learning model 1250 which outputs intra-operative navigated guidance data for computer assisted navigation during surgery. FIG. 12 also shows example training of the machine learning model 1250 according to some embodiments.

Referring to FIG. 12, the system is connected to one or more sensor circuits from which it obtains intra-operative tactile sensing data 1252 indicating a sensed characteristic of a tool contacting a location on patient anatomy within a surgical site. A machine learning model 1250 processes the intra-operative tactile sensing data 1252, which may be pre-processed and conditioned beforehand, to generate intra-operative navigated guidance data. The intra-operative navigated guidance data is provided to an intra-operative guidance component 1226. The intra-operative guidance component 1226 may provide computer generated graphical and/or textual guidance to a surgeon and/or may use the intra-operative navigated guidance data to adjust (adapt) movement of the tool by a surgical robot 100 which is controlled pursuant to a pre-operative surgical plan.

The machine learning model 1250 may be hosted by the computer platform 400 and be part of the spinal surgery navigation system 1220 illustrated in FIG. 11, in accordance with some embodiments.

Figure 13:
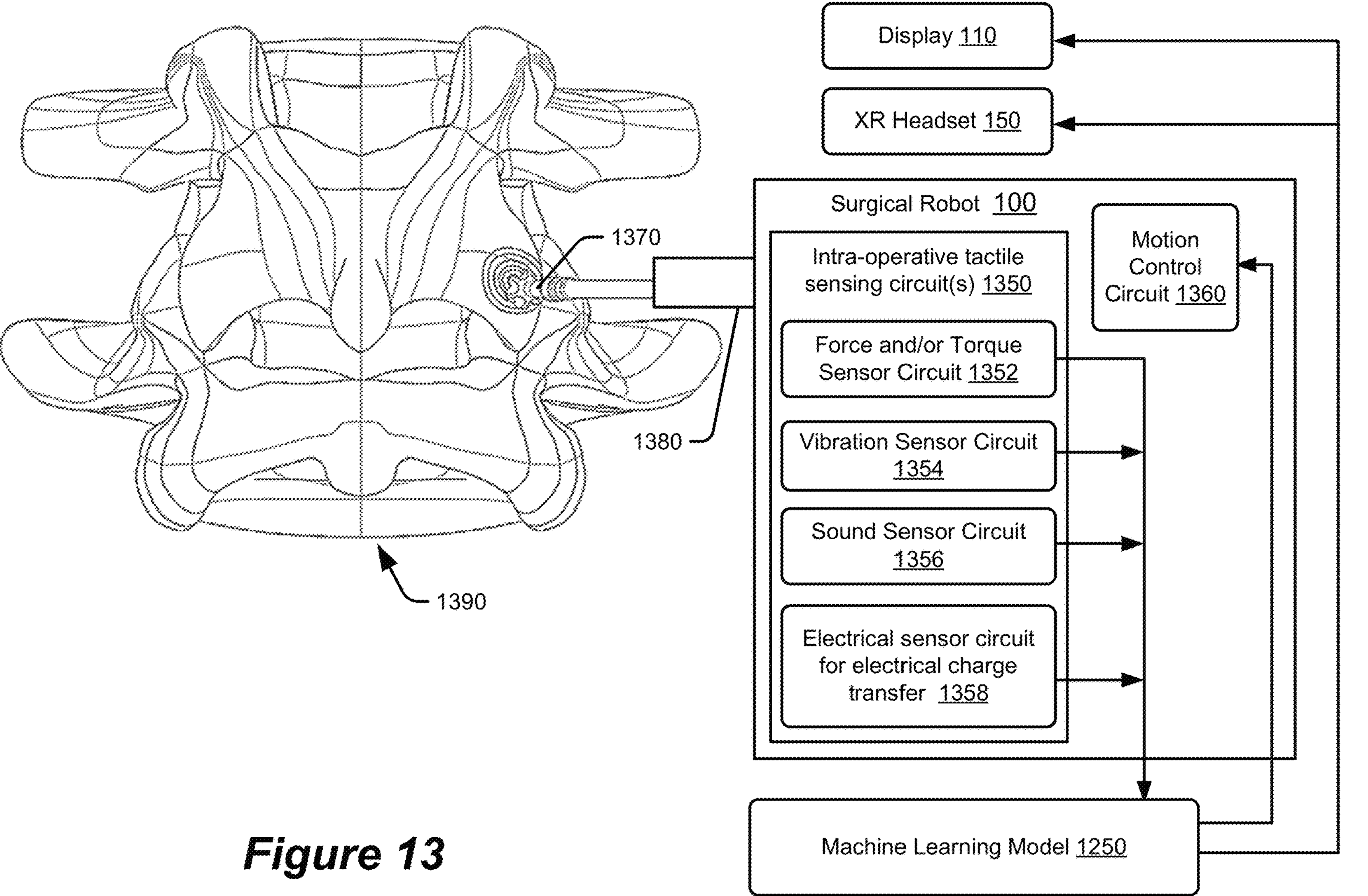
FIG. 13 illustrates another block diagram of the surgery navigation system of FIG. 12 including example types of intra-operative tactile sensing circuits which sense characteristics of a tool working on a vertebral body and provide input to the machine learning model according to some embodiments.

FIG. 13 illustrates another block diagram of the surgery navigation system which includes example types of intra-operative tactile sensing circuits 1350 that are operative to sense certain characteristics of a tool 1370 working on a vertebral body 1390 for input to the machine learning model 1250 of FIG. 12 according to some embodiments. The intra-operative tactile sensing circuits 1350 may be used with or be part of the surgery navigation system illustrated in FIG. 12.

Referring to FIGS. 12 and 13, the tool 1370 may be any type of surgical tool, including but not limiting to, a burr, awl, saw, drill, bone scraper, chisel, pliers, probe, or other tool which may or not be configured to probe or remove bone, soft tissue, or other biological components. In the illustrated non-limiting example of FIG. 13, the tool 1370 is connected to be rotated by a motor assembly 1380. The motor assembly 1380 may be positioned and moved by a surgeon who is being provided computer navigated guidance based on the intra-operative navigated guidance data. Alternatively, as shown in FIG. 13, the motor assembly 1380 may be connected through the end-effector 112 to the robot arm 104 (e.g., FIGS. 8-11) of the surgical robot 100. The surgical robot 100 may operate to guide movement of the tool 1370 based on the intra-operative navigated guidance data from the machine learning model 1250 and based on tool tracking data 1254 from the camera tracking system 200 (e.g., FIGS. 8-11) indicating pose of the tool 1370 relative to the patient anatomy. Moreover, the surgical robot 100 may guide movement of the tool 1370 based on a surgical plan 1256.

The intra-operative tactile sensing circuit(s) 1350 are configured to provide intra-operative tactile sensing data 1252 to the machine learning model 1250 that is indicative of a sensed characteristic of a tool contacting a location on patient anatomy within a surgical site.

In one embodiment, a force sensor circuit 1352 provides data indicating a level of force between the tool 1370 and the location on the patient anatomy. In another embodiment, a torque sensor circuit 1352 provides data indicating a level of torque between the tool 1370 and the location on the patient anatomy.

In another embodiment, a vibration sensor circuit 1354 provides data indicating a vibration characteristic of the tool 1370 working on the patient anatomy. The data may for example, indicate amplitude and/or frequency of one or more vibrational modes of the tool 1370.

In another embodiment, a sound sensor circuit 1356 provides data indicating a sound characteristic of the tool 1370 working on the patient anatomy. The data may for example, indicate amplitude and/or frequency of one or more components of the sound generated by the tool 1370 working on the patient anatomy.

In another embodiment, an electrical sensor circuit 1358 provides data indicating electrical charge transfer and/or impedance between the tool and the location on the patient anatomy, which can be. The data may for example, electrical charge transfer characteristics (e.g., current, voltage, power, etc.) and/or impedance characteristics from the tool 1370 to the patient anatomy contacted by the tool 1370.

The machine learning model 1250 processes output of the intra-operative tactile sensing data 1252 from the sensing circuits 1350 to generate the intra-operative navigated guidance data, which may identify and differentiate between contact with bone, cartilage, ligaments, or other soft tissue including but not limited to the nucleus pulposus and annulus fibrosis.

For example, the machine learning model 1250 may identify when the tool 1370 tip moves from bone to soft tissue or void, and/or vice-versa from soft tissue to bone, and provide that indication as part of the intra-operative navigated guidance data. Feedback on the presently sensed force, torque, vibrations, sound, electrical charge transfer, and/or electrical impedance can be processed through the machine learning model 1250 as part of a tactile feedback navigation loop while the tool is used during a surgical procedure.

The machine learning model 1250 may process the intra-operative tactile sensing data to generate the intra-operative navigated guidance data based on the indicated level of force and/or the indicated level of torque on the tool 1370 working on the patient anatomy. For example, identification of the type of biological material being worked on the tool 1370 and/or identification of progress of the tool 1370 through biological material may be based on the machine learning model 1250 having been trained based on training data of measurements of force and/or torque levels of the same or similar tools during earlier logged surgeries, and based on associated logs of tracked poses relative to anatomy and relative to surgical plans.

Additionally or alternatively, the machine learning model 1250 may process the intra-operative tactile sensing data to generate the intra-operative navigated guidance data based on the indicated vibration characteristic. The machine learning model 1250 may be configured to process an indication of the amplitude and/or frequency of one or more vibrational modes of the tool 1370 working on the patient anatomy. For example, identification of the type of biological material being worked on the tool 1370 and/or identification of progress of the tool 1370 through biological material may be based on the machine learning model 1250 having been trained based on training data of measurements of vibration characteristics of the same or similar tools during earlier logged surgeries, and based on associated logs of tracked poses relative to anatomy and relative to surgical plans.

Additionally or alternatively, the machine learning model 1250 may process the intra-operative tactile sensing data to generate the intra-operative navigated guidance data based on the indicated sound characteristic. The machine learning model 1250 may be configured to process an indication of the amplitude and/or frequency of one or more components of the sound generated by the tool 1370 working on the patient anatomy. For example, identification of the type of biological material being worked on the tool 1370 and/or identification of progress of the tool 1370 through biological material may be based on the machine learning model 1250 having been trained based on training data of measurements of characteristics of components of sound generated by the same or similar tools during earlier logged surgeries, and based on associated logs of tracked poses relative to anatomy and relative to surgical plans.

Additionally or alternatively, the machine learning model 1250 may process the intra-operative tactile sensing data to generate the intra-operative navigated guidance data based on the indicated electrical charge transfer characteristic and/or an impedance characteristic. The machine learning model 1250 may be configured to process an indication of the electrical charge transfer characteristic and/or an impedance characteristic between the tool 1370 and the location on the patient anatomy. For example, identification of the type of biological material being worked on the tool 1370 and/or identification of progress of the tool 1370 through biological material may be based on the machine learning model 1250 having been trained based on training data of measurements of characteristics of the electrical charge transfer and/or impedance through the same or similar tools during earlier logged surgeries, and based on associated logs of tracked poses relative to anatomy and relative to surgical plans.

For example, during access and decompression on a spine, the surgical robot 100 may operate to identify progress of the tool 1370 burring through cortical or cancellous bone, and/or to identify what type of biological components (bone, cartilage, ligaments, or other soft tissue including but not limited to the nucleus pulposus and annulus fibrosis) are primarily being worked on by the tool 1370. For instance, during facet removal, as a surgeon advances in the workflow the surgical robot 100 can operate to identify the stages of cutting through cortical bone, cutting through cancellous bone sensing as the density decreases, cutting through cartilage and synovial membrane sensing as the fact capsule deteriorates, and cutting through cortical bone and the ligamentum flavum sensing when the facet joint becomes released. Along each of these landmark steps of the burring, the surgical robot 100 would provide cues to prevent the surgeon from plunging or skiving off trajectory. The cues would range from audio or visual signals for the surgeon to observe while operating, or even go so far as to be physical cues such as a computer controlled off switch for the tool 1370.

Processing circuitry, e.g., computer platform 400 (FIG. 11), can be operative to obtain tool tracking data indicating pose of the tool relative to the patient anatomy (e.g., from the camera tracking system (FIGS. 8-11), and process the tool tracking data 1254 and the intra-operative tactile sensing data through the machine learning model 1250 to generate the intra-operative navigated guidance data. The processing circuitry may further obtain pre-operative patient data and a surgical plan 1256 defining location of a region of the patient anatomy indicated in the pre-operative patient data that is to be removed, and process the surgical plan, the tool tracking data 1254, and the pre-operative patient data through the machine learning model 1250 to generate the intra-operative navigated guidance data to include plan progress information characterizing what portion of the region of the patient anatomy has been removed according to the surgical plan.

The machine learning model 1250 may be configured to check navigated landmarks by, for example, comparing location of a landmark identified in a pre-operative patient image (e.g., edge region of a bone) to location of the tool 1370 when the intra-operative tactile sensing data 1252 indicates the tool 1370 is at the landmark (e.g., the data 1252 indicates progression of the tool 1370 through soft tissue to contact the edge region of the bone). Similarly, the machine learning model 1250 may be configured to more continuously check integrity of navigated landmarks by, for example, monitoring whether the intra-operative navigated guidance data indicates that the tool 1370 is currently working on a type of biological material which is expected to be present where the tracked tool 1370 is located on the patient anatomy according to the patient data (e.g., fluoroscopy image(s)).

When the surgical robot 100 is used in a surgical procedure, processing circuitry (e.g., the motion control circuit 1360 in FIG. 13) can operate to control movement of the tool 1370 by the robot arm 104 of the surgical robot 100 based on the plan progress information to direct the tool 1370 toward a remaining portion of the region of the patient anatomy to be removed according to the surgical plan. The intra-operative navigated guidance data may be processed by a motion control circuit 1360 to control movement of the tool 1370 by one or motors of the surgical robot 100. The motion control circuit 1360 may for example, slow down movement or stop movement of the tool 1370 along a planned trajectory responsive to the intra-operative navigated guidance data indicating that the tool 1370 is passing through or has passed through a defined biological material, e.g., passed through bone into soft tissue.

With further reference to FIG. 12, example operations that may be performed by a training module 1258 to train the machine learning model 1250 are explained.

During surgery, processing circuitry can operate to obtain pre-operative patient data and the surgical plan 1256 defining location of a region of the patient anatomy indicated in the pre-operative patient data that is to be removed. The processing circuitry can obtain tool tracking data 1254 indicating the real-time pose of the tool relative to the patient anatomy. The processing circuitry can process the intra-operative tactile sensing data, the tool tracking data, the surgical plan, and the pre-operative patient data through the machine learning model to generate the intra-operative navigated guidance data. As described above, the surgeon can be provided computer surgical navigation based on the intra-operative navigated guidance data and/or movement of the tool 1370 by the surgical robot 100 can be controlled based on the intra-operative navigated guidance data.

In the illustration of FIG. 13, the intra-operative navigated guidance data can be provided to a display device 110 and/or an XR headset 150, such as the displays and XR headsets illustrated in FIG. 8-11. The XR headset 150 can include at least one see-through display device, and processing circuitry is operative to control the see-through display device to display information to guide operator movement of the tool based on the intra-operative navigated guidance data.

Following the surgery, the training module 1258 can train the machine learning model 1250 based on the pre-operative and intra-operative data collected during the surgery. In one embodiment, the processing circuitry of the training module 1258 can obtain patient post-operative feedback data characterizing deviation between the surgical plan and an intra-operative surgery process which was performed on the patient responsive to the intra-operative navigated guidance data. For example, the patient post-operative feedback data may characterize deviation between planned movement of the tool 1370 according to surgical plan and the intra-operative tracked movement of the tool 1370 contained in an intra-operative data log. The processing circuitry of the training module 1258 can then train the machine learning model 1250 based on the patient post-operative feedback data. Thus, for example, when the tool 1370 is moved along intra-operative tracked trajectory(ies) in a manner that deviates from what was defined by the surgical plan, such as due to intervention or guidance from the surgeon, the machine learning model 1250 can be trained so that in the future it would more closely perform according to the intra-operative tracked trajectory(ies) when presented with a same or similar surgical plan and a same or similar patient anatomy.

The patient post-operative feedback data may for example, characterize one or more of: post-operative measurements of disc material removed from the spine of the patient; post-operative measurements of spinal fusion rate of the patient; post-operative measurements of spine decompression of the patient; and post-operative measurements of spinal deformation of the patient. Thus, for example, the machine learning model 1250 can be trained based on indications in the patient post-operative feedback data of how closely the amount of disc material that was removed satisfies the surgical plan 1256, how closely the spinal fusion rate measured for the patient satisfies what was expected for the surgical plan 1256, how closely the spine decompression measured for the patient satisfies what was expected for the surgical plan 1256, and/or how closely the spinal deformation measured for the patient satisfies what was expected for the surgical plan 1256.

In accordance with some embodiments, the surgery navigation system includes a plurality of the sensor circuits, and at least two of the sensor circuits are different ones of: a force sensor operative to output an indication of level of force between the tool and the location on the patient anatomy; a torque sensor operative to output an indication of level of torque between the tool and the location on the patient anatomy; vibration sensor operative to output a vibration characteristic of the tool working at the location on the patient anatomy; sound sensor operative to output a sound characteristic of the tool working at the location on the patient anatomy; and an electrical sensor operative to output an electrical charge transfer characteristic and/or an impedance characteristic between the tool and the location on the patient anatomy. The machine learning model 1250 includes a neural network component (e.g., 1310 in FIG. 2) including an input layer having input nodes, a sequence of hidden layers each having a plurality of combining nodes, and an output layer having output nodes. At least one processing circuit operates to provide outputs of the sensor circuits to different ones of the input nodes of the neural network model, and to generate the intra-operative navigated guidance data based on output of output nodes of the neural network component. The feedback training component 1258 is configured to adapt weights and/or firing thresholds used by the combining nodes of the neural network component based on patient post-operative feedback data.

Some further embodiments are directed to tracking progress of the tool 1370 according to the surgical plan 1256. These embodiments can use a probe, which may be part of the tool 1370 or may be a separate device, to identify locations where bone is exposed, locations where soft tissue is exposed, and locations where a void occurs. The probe can be vibrationally excited as it is moved to probe locations at a surgical site, and intra-operative tactile sensing circuits can provide sensed characteristics to the machine learning model 1250 to, for example, identify and differentiate between contact with bone, cartilage, ligaments, or other soft tissue including but not limited to the nucleus pulposus and annulus fibrosis. Example operations according to some embodiments are explained in the context illustrated in FIGS. 14 and 15.

Figure 14:
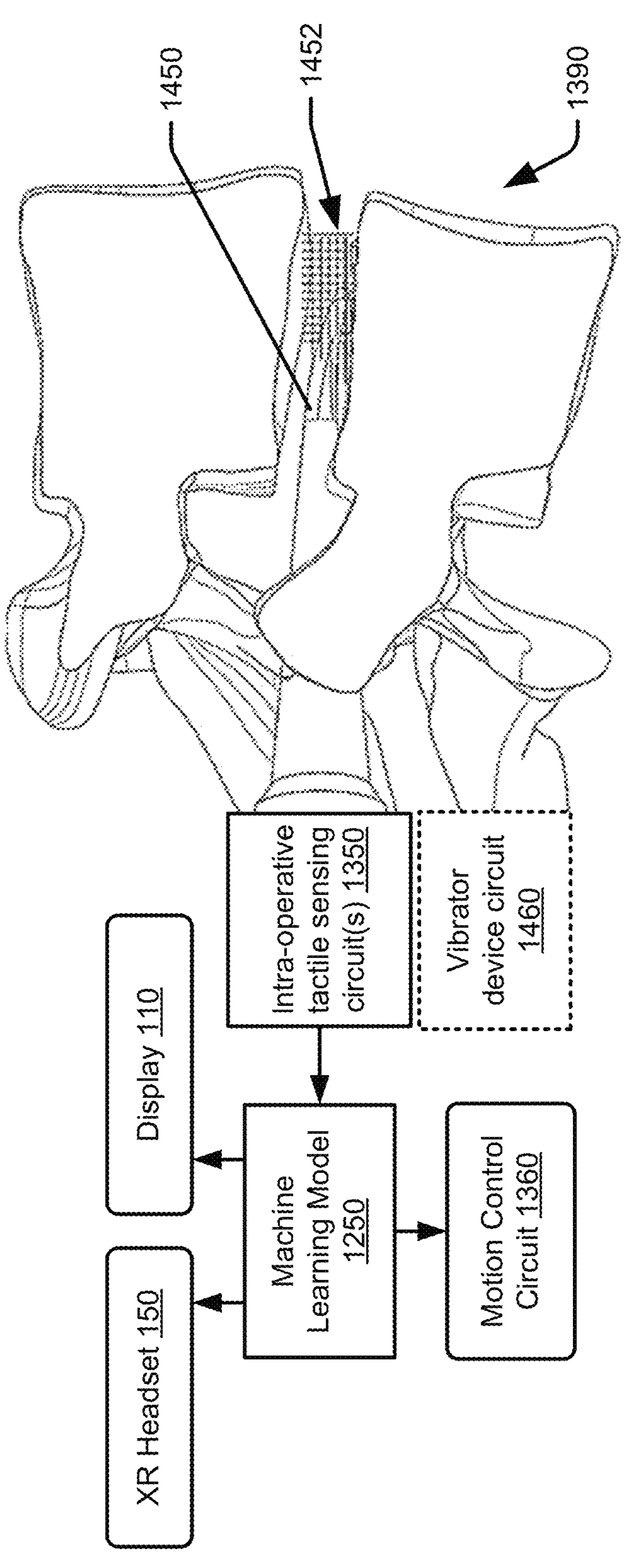
FIG. 14 illustrates another block diagram of the surgery navigation system of FIG. 12 or 13 with an intra-operative tactile sensing circuit outputting a sensed characteristic of a probe having a tip vibrationally excited and inserted into intradiscal space between vertebral bodies, and where the outputted characteristic is provided to the machine learning model to identify locations where the probe is contacting bone versus soft tissue, according to some embodiments.
Figure 15:
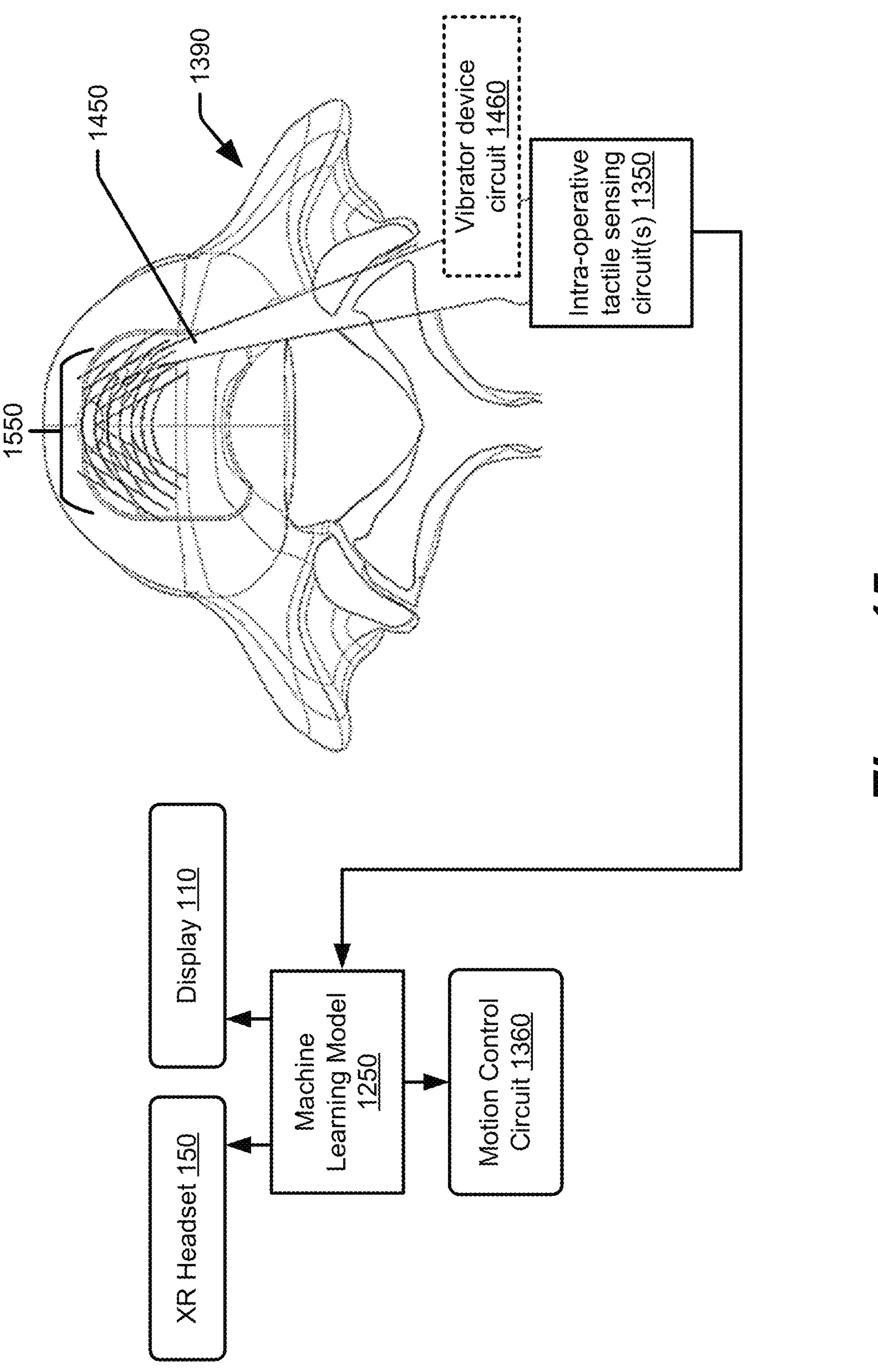
FIG. 15 illustrates another block diagram of the surgery navigation system and shows another view of the probe of FIG. 14 with the tip inserted into the intradiscal space between vertebral bodies according to some embodiments.

FIG. 14 illustrates another block diagram of the surgery navigation system of FIG. 12 or 13 with an intra-operative tactile sensing circuit 1350 outputting a sensed characteristic of a probe 1450 which has a tip that is vibrationally excited and inserted into intradiscal space 1452 between vertebral bodies 1390. The outputted characteristic is provided to the machine learning model 1250 to identify locations where the probe is contacting bone versus soft tissue and/or to identify and differentiate between contact with different types of biological materials according to some embodiments. FIG. 15 illustrates another block diagram of the surgery navigation system and shows another view of the probe 1450 of FIG. 14 with the tip inserted into the intradiscal between the vertebral bodies 1390 according to some embodiments.

Referring to FIGS. 14 and 15, a vibrator device 1460 is connected to the probe 1450 and operative to vibrationally excite a tip of the probe 1450. The vibrator device 1460 may for example, be connected to a base of the probe 1450, elsewhere along a shaft of the probe 1450, or at the tip of the probe 1450. The vibrator device 1460 may include a rotating offset weight and/or a pulsed piezoelectric device to vibrationally excite the probe 1450. An intra-operative tactile sensing circuit 1350, e.g., a vibration sensor, is connected directly or indirectly to the probe 1450 to output a vibration signal indicating a vibration characteristic of the tip of the probe 1450 contacting the location on the patient anatomy while the tip is vibrationally excited by the vibrator device 1460. Processing circuitry is operative to process the vibration characteristic indicated by the vibration signal through the machine learning model 1250 to generate the intra-operative navigated guidance data to indicate locations where the probe 1450 is contacting bone versus soft tissue of the patient anatomy.

In some embodiments, the processing circuitry is operative to determine from the intra-operative navigated guidance data, completed locations within the intradiscal space 1452 between the interior and superior vertebral bodies 1390 where anatomical material has been removed according to the surgical plan 1256. The processing circuitry may operate to move the probe 1450 about the surgical site testing where anatomical material has been removed, and may determine where to probe based on the surgical plan 1256. The processing circuitry is operative to control movement of the tool 1370 by the arm 102/104 of the surgical robot 100, e.g., via the motion control circuit 1360, based on the completed locations to direct the tool toward a remaining portion of the anatomical material to be removed according to the surgical plan 1256.

In some embodiments, the processing circuitry is operative to determine from the intra-operative navigated guidance data, completed locations within the intradiscal space 1452 between the vertebral bodies 1390 where anatomical material has been removed according to the surgical plan 1256, and control a display device based on the completed locations and the surgical plan, to display a graphical indication of where anatomical material has been removed from the intradiscal space 1452 and where anatomical material remains to be removed from the intradiscal space 1452 according to the surgical plan 1256. For example, the processing circuitry may control the display 110 and/or the XR headset 150 to display a graphical indication of location of anatomical material that should be removed according to the surgical plan 1256. The graphical indication may be rendered as the cross-hatched lines in area 1550 illustrated in FIG. 15, or may be rendered as another graphical indication using shading, texture, color, symbols, shapes, etc. to indicate where anatomical material has been removed and/or remains to be removed according to the surgical plan 1256.

As explained above, the intra-operative navigated guidance data generated by the machine learning model can be used to control movement of the surgical robot 100.

A tracking sub-system (e.g., the camera tracking system 200 of FIG. 11) can be operative to determine pose of the tool relative to pose of the patient anatomy in a defined coordinate system. Processing circuitry (e.g., computer platform 400 of FIG. 11) is operative to obtain a surgery plan, determine a target pose of the tool based on the surgery plan indicating where a surgical procedure is to be performed on the patient anatomy, and generate the intra-operative navigated guidance data based on comparison of the determined pose of the tool and the target pose of the tool, and based on output of the machine learning model from processing the intra-operative tactile sensing data.

As explained above, a surgical robot can include a robot base, a robot arm connected to the robot base and configured to guide movement of the tool, and at least one motor operatively connected to control movement of the robot arm relative to the robot base. Processing circuitry is operative to obtain pre-operative patient data and a surgical plan defining a surgical procedure to be performed on the patient anatomy indicated in the pre-operative patient data. The processing circuitry is operative to obtain tool tracking data indicating pose of the tool relative to the patient anatomy, and to process the tool tracking data, the surgical plan, and the pre-operative patient data through the machine learning model to generate the intra-operative navigated guidance data. The processing circuitry is operative to control movement of the at least one motor based on the intra-operative navigated guidance data to guide movement of the tool.

Through these and other embodiments disclosed herein, improved surgery outcomes may be obtained through processing of intra-operative tactile sensing data through a machine learning model to generate intra-operative navigated guidance data, and providing the intra-operative navigated guidance data to a display device for navigation use by a surgeon during a surgical procedure and/or to a surgical robot to control movement of a tool during the surgical procedure.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A surgery navigation system for computer assisted navigation during surgery, the surgery navigation system comprising:

a processing circuitry;

a tool for performing a surgery and having a sensor circuit positioned proximate to a working potion of the tool for sensing tactile sensing data;

a machine learning model that has been trained with collected intra-operative tactile sensing data;

the processing circuitry configured to:

obtain from the sensor circuit, intra-operative tactile sensing data indicating a sensed characteristic of the tool contacting a location on patient anatomy within a surgical site;

process the intra-operative tactile sensing data through the trained machine learning model to generate intra-operative navigated guidance data including a level of force between the tool and the location on the patient anatomy; and provide the intra-operative navigated guidance data to a display device and/or to a surgical robot to control movement of the tool, wherein the intra-operative navigated guidance data controls movement of the tool through the surgical robot.

2. The surgery navigation system of claim 1, wherein the sensor circuit comprises a force sensor and/or torque sensor, and wherein operation of the processing circuitry to process the intra-operative tactile sensing data through the machine learning model to generate intra-operative navigated guidance data, comprises to:

determine from output of the force sensor and/or torque sensor, a level of force between the tool and the location on the patient anatomy and/or a level of torque between the tool and the location on the patient anatomy; and process the level of force and/or the level of torque through the machine learning model to generate the intra-operative navigated guidance data to characterize progress of the tool through soft tissue and/or bone of the patient anatomy.

3. The surgery navigation system of claim 1, wherein the sensor circuit comprises a vibration sensor, wherein operation of the processing circuitry to process the intra-operative tactile sensing data through the machine learning model to generate intra-operative navigated guidance data, comprises to:

determine from output of the vibration sensor, a vibration characteristic of the tool working at the location on the patient anatomy; and process the vibration characteristic through the machine learning model to generate the intra-operative navigated guidance data to characterize progress of the tool through soft tissue and/or bone of the patient anatomy.

4. The surgery navigation system of claim 1, wherein the sensor circuit comprises a sound sensor, wherein operation of the processing circuitry to process the intra-operative tactile sensing data through the machine learning model to generate intra-operative navigated guidance data, comprises to:

determine from output of the sound sensor, a sound characteristic of the tool working at the location on the patient anatomy; and process the sound characteristic through the machine learning model to generate the intra-operative navigated guidance data to characterize progress of the tool through soft tissue and/or bone of the patient anatomy.

5. The surgery navigation system of claim 1, wherein the sensor circuit comprises an electrical sensor configured to sense electrical charge transfer and/or impedance between the tool and the location on the patient anatomy, wherein operation of the processing circuitry to process the intra-operative tactile sensing data through the machine learning model to generate intra-operative navigated guidance data, comprises to:

determine from output of the electrical sensor, electrical charge transfer characteristics and/or impedance characteristics between the tool and the location on the patient anatomy; and process the electrical charge transfer characteristics and/or impedance characteristics through the machine learning model to generate the intra-operative navigated guidance data to characterize progress of the tool through soft tissue and/or bone of the patient anatomy.

6. The surgery navigation system of claim 1, wherein the processing circuitry is further operative to:

obtain tool tracking data indicating pose of the tool relative to the patient anatomy; and process the tool tracking data and the intra-operative tactile sensing data through the machine learning model to generate the intra-operative navigated guidance data.

7. The surgery navigation system of claim 6, wherein the processing circuitry is further operative to:

obtain pre-operative patient data and a surgical plan defining location of a region of the patient anatomy indicated in the pre-operative patient data that is to be removed; and process the surgical plan, the tool tracking data, and the pre-operative patient data through the machine learning model to generate the intra-operative navigated guidance data to include plan progress information characterizing what portion of the region of the patient anatomy has been removed according to the surgical plan.

8. The surgery navigation system of claim 7, wherein the processing circuitry is further operative to:

control movement of the tool by a robot arm of the surgical robot based on the plan progress information to direct the tool toward a remaining portion of the region of the patient anatomy to be removed according to the surgical plan.

9. The surgery navigation system of claim 7, wherein the processing circuitry is further operative to:

control a display device based on the plan progress information to display a graphical indication of a remaining portion of the region of the patient anatomy to be removed according to the surgical plan.

10. The surgery navigation system of claim 1, further comprising:

an extended reality (XR) headset including at least one see-through display device, wherein the processing circuitry is operative to control the see-through display device to display information to guide operator movement of the tool based on the intra-operative navigated guidance data.

11. The surgical navigation system of claim 1, further comprising:

a vibrator device connected to a probe and operative to vibrationally excite a tip of the probe;

a vibration sensor connected to output a vibration signal indicating a vibration characteristic of the tip of the probe contacting the location on the patient anatomy while the tip is vibrationally excited by the vibrator device;

wherein the processing circuitry is further operative to process the vibration characteristic indicated by the vibration signal through the machine learning model to generate the intra-operative navigated guidance data to indicate locations where the probe is contacting bone versus soft tissue of the patient anatomy.

12. The surgical navigation system of claim 11, wherein the processing circuitry is further operative to:

determine from the intra-operative navigated guidance data, completed locations within an intradiscal space between interior and superior vertebral bodies where anatomical material has been removed according to a surgical plan; and control movement of the tool by an arm of the surgical robot based on the completed locations to direct the tool toward a remaining portion of the anatomical material to be removed according to the surgical plan.

13. The surgical navigation system of claim 11, wherein the processing circuitry is further operative to:

determine from the intra-operative navigated guidance data, completed locations within an intradiscal space between interior and superior vertebral bodies where anatomical material has been removed according to a surgical plan; and control a display device based on the completed locations and the surgical plan, to display a graphical indication of where anatomical material has been removed from the intradiscal space and where anatomical material remains to be removed from the intradiscal space according to the surgical plan.

14. The surgery navigation system of claim 1, wherein the processing circuitry is further operative to:

obtain pre-operative patient data and a surgical plan defining location of a region of the patient anatomy indicated in the pre-operative patient data that is to be removed;

obtain tool tracking data indicating pose of the tool relative to the patient anatomy;

process the intra-operative tactile sensing data, the tool tracking data, the surgical plan, and the pre-operative patient data through the machine learning model to generate the intra-operative navigated guidance data;

obtain patient post-operative feedback data characterizing deviation between the surgical plan and an intra-operative surgery process which was performed on the patient responsive to the intra-operative navigated guidance data; and train the machine learning model based on the patient post-operative feedback data.

15. The surgery navigation system of claim 1, wherein the processing circuitry is further operative to:

obtain patient post-operative feedback data characterizing at least one of post-operative measurements of disc material removed from the spine of the patient, post-operative measurements of spinal fusion rate of the patient, post-operative measurements of spine decompression of the patient, and post-operative measurements of spinal deformation of the patient; and train the machine learning model based on the patient post-operative feedback data.

16. The surgery navigation system of claim 1, wherein the surgery navigation system comprises a plurality of the sensor circuits, and at least two of the sensor circuits are different ones of: a force sensor operative to output an indication of level of force between the tool and the location on the patient anatomy; a torque sensor operative to output an indication of level of torque between the tool and the location on the patient anatomy; vibration sensor operative to output a vibration characteristic of the tool working at the location on the patient anatomy; sound sensor operative to output a sound characteristic of the tool working at the location on the patient anatomy; and an electrical sensor operative to output an electrical charge transfer characteristic and/or an impedance characteristic between the tool and the location on the patient anatomy; and wherein the machine learning model comprises:

a neural network component including an input layer having input nodes, a sequence of hidden layers each having a plurality of combining nodes, and an output layer having output nodes;

at least one processing circuit configured to provide outputs of the sensor circuits to different ones of the input nodes of the neural network model, and to generate the intra-operative navigated guidance data based on output of output nodes of the neural network component; and a feedback training component configured to adapt weights and/or firing thresholds used by the combining nodes of the neural network component based on patient post-operative feedback data.

17. The surgery navigation system of claim 1, further comprising:

a tracking sub-system operative to determine pose of the tool relative to pose of the patient anatomy in a defined coordinate system, wherein the processing circuitry is further operative to obtain a surgery plan, determine a target pose of the tool based on the surgery plan indicating where a surgical procedure is to be performed on the patient anatomy, and generate the intra-operative navigated guidance data based on comparison of the determined pose of the tool and the target pose of the tool, and based on output of the machine learning model from processing the intra-operative tactile sensing data.

18. The surgery navigation system of claim 1, further comprising:

the surgical robot including a robot base, a robot arm connected to the robot base and configured to guide movement of the tool, and at least one motor operatively connected to control movement of the robot arm relative to the robot base, wherein the processing circuitry is further operative to obtain pre-operative patient data and a surgical plan defining a surgical procedure to be performed on the patient anatomy indicated in the pre-operative patient data;

obtain tool tracking data indicating pose of the tool relative to the patient anatomy;

process the tool tracking data, the surgical plan, and the pre-operative patient data through the machine learning model to generate the intra-operative navigated guidance data;

control movement of the at least one motor based on the intra-operative navigated guidance data to guide movement of the tool.

19. A method by a surgery navigation system for computer assisted navigation during surgery, the method comprising:

training a machine learning model with intra-operative tactile sensing data that have been collected from previous surgeries;

obtaining from a sensor circuit positioned proximate to a working potion of a tool, intra-operative tactile sensing data indicating a sensed characteristic of the tool contacting a location on patient anatomy within a surgical site;

processing the intra-operative tactile sensing data through the trained machine learning model to generate intra-operative navigated guidance data including a level of force between the tool and the location on the patient anatomy; and providing the intra-operative navigated guidance data to a display device and/or to a surgical robot controlling movement of the tool, wherein the intra-operative navigated guidance data controls movement of the tool through the surgical robot.

20. A computer program product comprising:

a non-transitory computer readable medium storing instructions executable by processing circuitry of a surgery navigation system for computer assisted navigation during surgery, the processing circuitry when executing the instructions is operative to:

obtain from a sensor circuit, intra-operative tactile sensing data indicating a sensed characteristic of a tool contacting a location on patient anatomy within a surgical site;

process the intra-operative tactile sensing data through a machine learning model that has been trained with intra-operative tactile sensing data that have been collected from previous surgeries to generate intra-operative navigated guidance data including a level of force between the tool and the location on the patient anatomy; and provide the intra-operative navigated guidance data to a display device and/or to a surgical robot to control movement of the tool, wherein the intra-operative navigated guidance data controls movement of the tool through the surgical robot, and wherein the sensor circuit if positioned proximate to a working potion of the tool.

* * * * *